(12) United States Patent
Zhou et al.

(10) Patent No.: US 9,745,345 B2
(45) Date of Patent: Aug. 29, 2017

(54) ANTI-TUMOR POLYPEPTIDES AND METHOD FOR PREPARING ANTI-TUMOR DRUGS COMPRISNG THE SAME

(71) Applicant: NANJING MEDICAL UNIVERSITY, Nanjing (CN)

(72) Inventors: Jianwei Zhou, Nanjing (CN); Jin Xu, Nanjing (CN); Xuan Li, Nanjing (CN); Aiping Li, Nanjing (CN)

(73) Assignee: NANJING MEDICAL UNIVERSITY, Nanjing (CN)

( * ) Notice: Subject to any disclaimer, the term of this patent is extended or adjusted under 35 U.S.C. 154(b) by 0 days.

(21) Appl. No.: 14/942,908

(22) Filed: Nov. 16, 2015

(65) Prior Publication Data

US 2016/0068570 A1    Mar. 10, 2016

Related U.S. Application Data

(63) Continuation-in-part of application No. PCT/CN2014/072461, filed on Feb. 24, 2014.

(30) Foreign Application Priority Data

May 14, 2013   (CN) .......................... 2013 1 0178099

(51) Int. Cl.
*C07K 7/06* (2006.01)
*C07K 7/08* (2006.01)
*A61K 38/00* (2006.01)
*C07K 14/47* (2006.01)

(52) U.S. Cl.
CPC ................. *C07K 7/06* (2013.01); *C07K 7/08* (2013.01); *C07K 14/4703* (2013.01); *A61K 38/00* (2013.01)

(58) Field of Classification Search
CPC ........ C07K 7/06; C07K 7/08; C07K 14/4703; A61K 38/00
See application file for complete search history.

(56) References Cited

U.S. PATENT DOCUMENTS 6,808,893 B1 * 10/2004 Rothstein ........... C12N 15/1138
435/320.1

OTHER PUBLICATIONS

Chen et al, JWA as a functional molecule to regulate cancer cells migration via MAPK cascades and F-actin cytoskeleton, Cellular Signalling, 2007, 19, pp. 1315-1327.*

* cited by examiner

*Primary Examiner* — Julie Ha
*Assistant Examiner* — Li Ni Komatsu
(74) *Attorney, Agent, or Firm* — Matthias Scholl P.C.; Matthias Scholl

(57) ABSTRACT

An anti-tumor polypeptide, having an amino acid sequence represented by FPGSDRF (SEQ ID NO: 15), X-FPGSDRF (SEQ ID NO: 16), FPGSDRF-Z (SEQ ID NO: 17), or X-FPGSDRF-Z (SEQ ID NO: 18) is disclosed. The various capital letters denote amino acids: F: phenylalanine; P: proline; G: glycine; D: aspartic acid; R: arginine; S is a phosphorylated serine residue, X and Z are an amino acid residue or an amino acid sequence, respectively, X is one selected from the group consisting of F, $(R)_9$ (SEQ ID NO: 19), $(R)_9$-F (SEQ ID NO: 20), 6-aminocaproic acid, 6-aminocaproic acid-F, 6-aminocaproic acid-$(R)_9$ (SEQ ID NO: 21), and 6-aminocaproic acid-$(R)_9$-F (SEQ ID NO: 22), Z is one selected from the group consisting of A, $(G)_n$-RGD (SEQ ID NO: 23), and A-$(G)_n$-RGD (SEQ ID NO: 24); and n is an integer greater than or equal to 0.

4 Claims, 15 Drawing Sheets

MDVNIAPLRAWDDITPGSDRFARPDFRDISKWNNRVVSNLLYYQTNYLVV ···· 50
AAMMISIVGFLSPENMILGGIVVVLVFTGFVWAAHNKDVLRRMKKRYPTT ···· 100
FVMVVMLASYFLISMFGGVMVFVFGITFPLLLMFIHASLRLRNLKNKLEN ···· 150
KMEGIGLKRTPMGIVLDALEQQEEGINRLTDYISKVKE ········ 188
FIG. 1
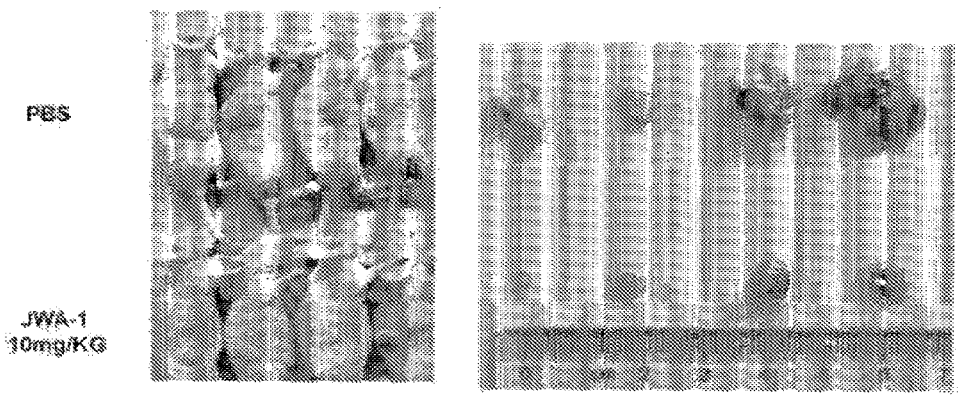
FIG. 2
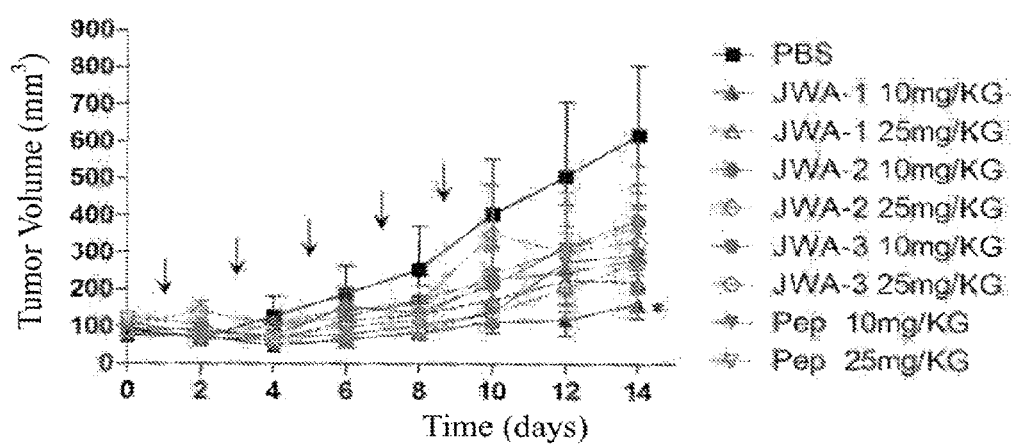
FIG. 3

US 9,745,345 B2

ANTI-TUMOR POLYPEPTIDES AND METHOD FOR PREPARING ANTI-TUMOR DRUGS COMPRISNG THE SAME

CROSS-REFERENCE TO RELATED APPLICATIONS

This application is a continuation-in-part of International Patent Application No. PCT/CN2014/072461 with an international filing date of Feb. 24, 2014, designating the United States, now pending, and further claims priority benefits to Chinese Patent Application No. 201310178099.X filed May 14, 2013. The contents of all of the aforementioned applications, including any intervening amendments thereto, are incorporated herein by reference.

BACKGROUND OF THE INVENTION

Field of the Invention

The invention relates to an anti-tumor polypeptide and a method for preparing an anti-tumor drug comprising the same.

Description of the Related Art

JWA gene, also known as ARL6IP5 (GenBank: AF070523.1, 1998; LOCUS: AF070523, NM_00640) was initially cloned from primary human tracheal-bronchial epithelial cells after all-trans-retinoic acid (ATRA) treatment, and it encodes a new type of cytoskeletal associated protein.

JWA protein can inhibit tumor cell adhesion, infiltration, angiogenesis and metastasis. It is imperative to apply JWA protein into clinical treatment. However, at present it is difficult to obtain purified JWA protein by using host expression system, which makes it impossible to conduct experiments with purified JWA protein in vivo and in vitro.

SUMMARY OF THE INVENTION

One objective of the invention is to screen and identify an anti-tumor peptide, which is derived from amino acid sequence of JWA protein. Another objective of the invention is to provide the application of this peptide for cancer treatment.

Inventors of this patent hold the view that purified JWA protein cannot be available due to the presence of its three transmembrane domains or other unknown reasons, thus limiting the investigation of JWA biological functions in vivo and in vitro. It is inferred by the inventors that the biological activity of JWA protein may be determined by a certain structural domain formed by several continuous amino acid residues in its primary structure, or by several non-continuous amino acid residues which are adjacent in the tertiary structure. The inventors have continued the research in depth on this basis and eventually screened and identified a JWA peptide with anti-tumor effect.

To achieve the above objective, in accordance with one embodiment of the invention, there is provided an anti-tumor polypeptide. An amino acid sequence of the polypeptide is represented by:

SEQ ID NO. 15: FPGSDRF;
X-FPGSDRF (SEQ ID NO: 16);
FPGSDRF-Z (SEQ ID NO: 17); or
X-FPGSDRF-Z (SEQ ID NO: 18);

wherein S is a phosphorylated serine residue; X and Z are an amino acid residue or an amino acid sequence, respectively;

X is one selected from the group consisting of F, $(R)_9$ (SEQ ID NO: 19), $(R)_9$-F (SEQ ID NO: 20), 6-aminocaproic acid, 6-aminocaproic acid-F, 6-aminocaproic acid-$(R)_9$ (SEQ ID NO: 21), and 6-aminocaproic acid-$(R)_9$-F (SEQ ID NO: 22);

Z is one selected from the group consisting of A, $(G)_n$-RGD (SEQ ID NO: 23), and A-$(G)_n$-RGD (SEQ ID NO: 24); and n is an integer greater than or equal to 0.

Z is one selected from the group consisting of A, $(G)_n$-RGD, and A-$(G)_n$-RGD; and n is an integer greater than or equal to 0.

In a class of this embodiment, n is between 0 and 10.

In a class of this embodiment, an N-terminus of the polypeptide is acetylated and a C-terminus of the polypeptide is amidated.

In accordance with one embodiment of the invention, there is provided a method for preparing an anti-tumor drug comprising using the above anti-tumor polypeptide.

In a class of this embodiment, the anti-tumor drug is for melanoma and gastric carcinoma.

Advantages of the anti-tumor polypeptide according to embodiments of the invention are summarized as follows: the polypeptide of the invention has a relatively short sequence for mass production. The polypeptide demonstrates significant anti-tumor activity at low dose. When combined with chemicals (such as arsenic trioxide, i.e. $As_2O_3$, ATO), the toxicity of the chemicals to tumor cells is increased. The polypeptide of the invention is not toxic to normal somatic cells and has a vast prospect of application.

BRIEF DESCRIPTION OF THE DRAWINGS

The invention is described hereinbelow with reference to the accompanying drawings, in which:

FIG. 1 is an amino acid sequence diagram of JWA protein. The underlined portions are transmembrane domains and the shaded portions are segments related to the embodiments, wherein the amino acids denoted by various letters are as follows: A: alanine; R: arginine; D: aspartic acid; Q: glutamine; E: glutamic acid; H: histidine; I: isoleucine; G: glycine; N: asparagine; L: leucine; K: lysine; M: methionine; F: phenylalanine; P: proline; S: serine; T: threonine; W: tryptophan; Y: tyrosine; V: valine;

FIG. 2 is a tumor formation comparison between the control group and the polypeptide JWA-1 (10 mg/kg) group in Example 2;

FIG. 3 is a graph of tumor volume changes in Example 2, wherein JWA1, JWA2, and JWA3 respectively denote three JWA single peptides, "pep" denotes an equivalent peptide blend of the three JWA single peptides, arrows denote drug administration times, and an asterisk * indicates P<0.05;

DETAILED DESCRIPTION OF THE EMBODIMENTS

Figure 4:
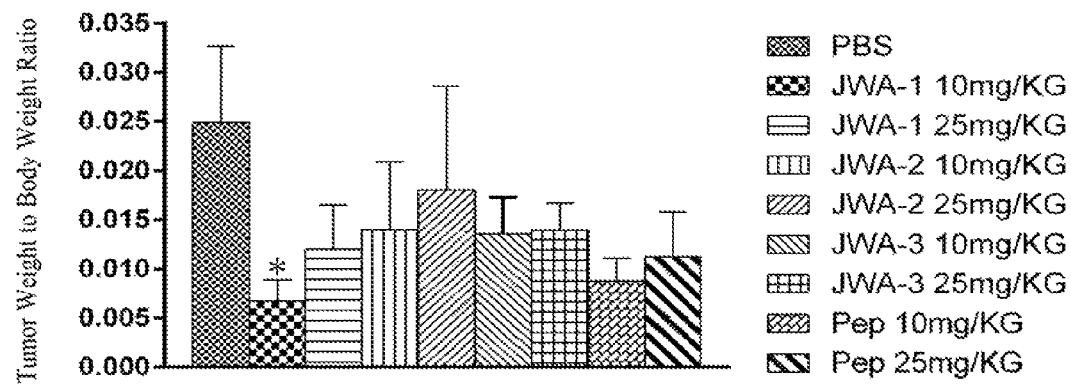
FIG. 4 is a tumor weight to body weight ratio graph of Example 2, wherein JWA1, JWA2, and JWA3 respectively denote three single JWA peptides, "pep" denotes an equivalent peptide blend of the three single JWA peptides, and an asterisk * indicates P<0.05.
Figure 5:
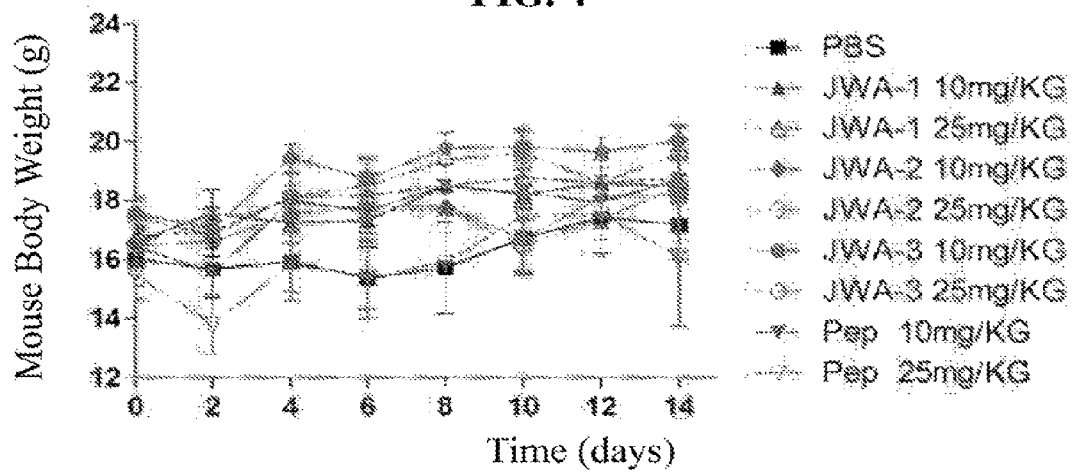
FIG. 5 is a graph of mouse body weight changes in Example 2, wherein JWA1, JWA2, and JWA3 respectively denote three single JWA peptides, and "pep" denotes an equivalent peptide blend of the three single JWA peptides.
Figure 6:
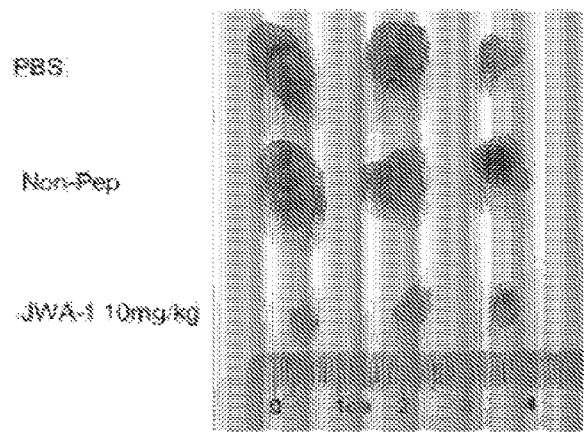
FIG. 6 is a tumor formation comparison among a control group, a non-pep group, and a polypeptide JWA-1 (10 mg/kg) group in Example 3.
Figure 7:
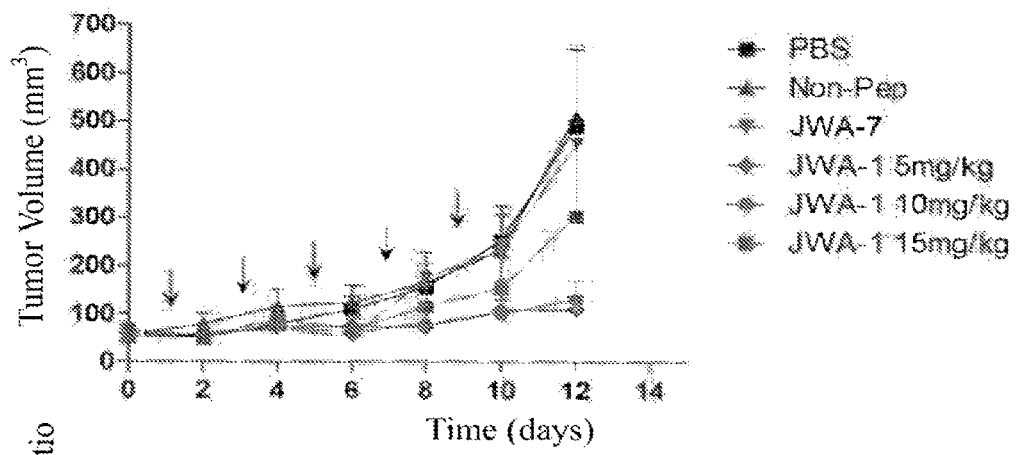
FIG. 7 is a graph of tumor volume changes in Example 3, wherein arrows denote drug administration times.
Figure 8:
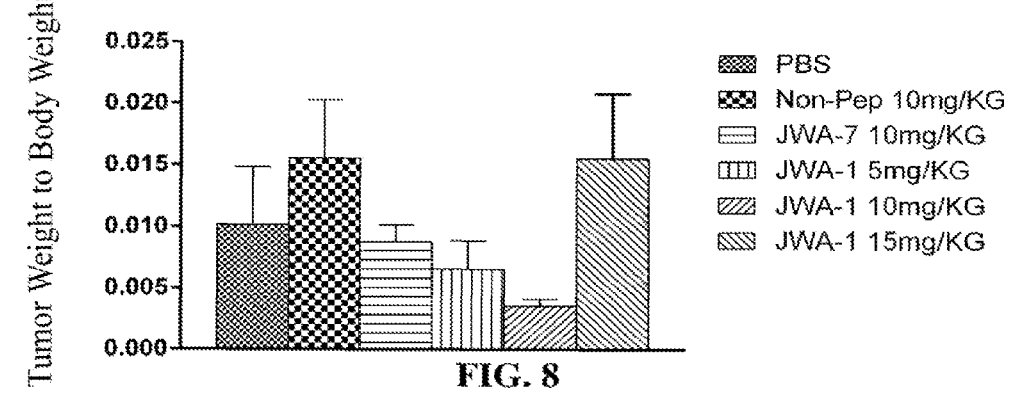
FIG. 8 is a tumor weight to body weight ratio graph of Example 3.
Figure 9:
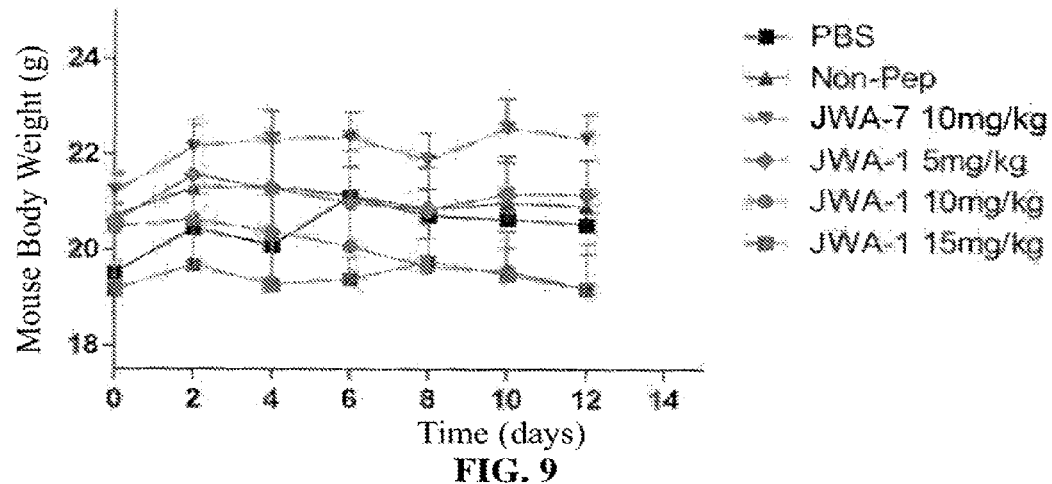
FIG. 9 is a graph of mouse body weight changes in Example 3.
Figure 10:
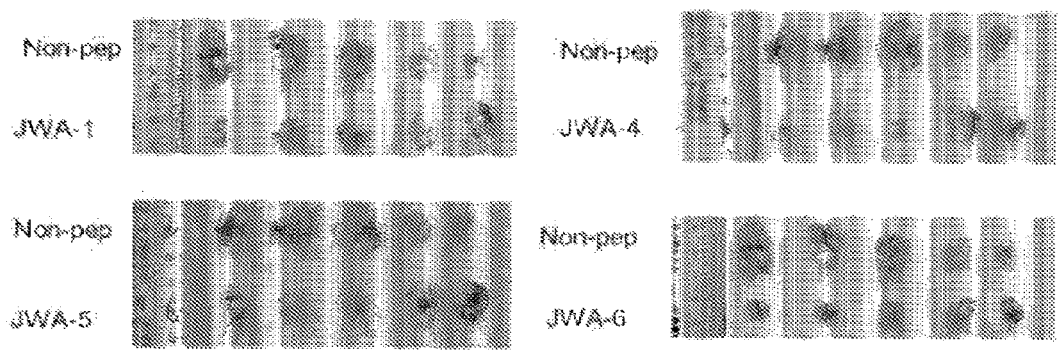
FIG. 10 is a tumor formation comparison among a non-pep group and a polypeptide JWA-1 (10 mg/kg) group, a polypeptide JWA-4 (10 mg/kg) group, a polypeptide JWA-5 (10 mg/kg) group, and a polypeptide JWA-6 (10 mg/kg) group, respectively in Example 4.
Figure 11:
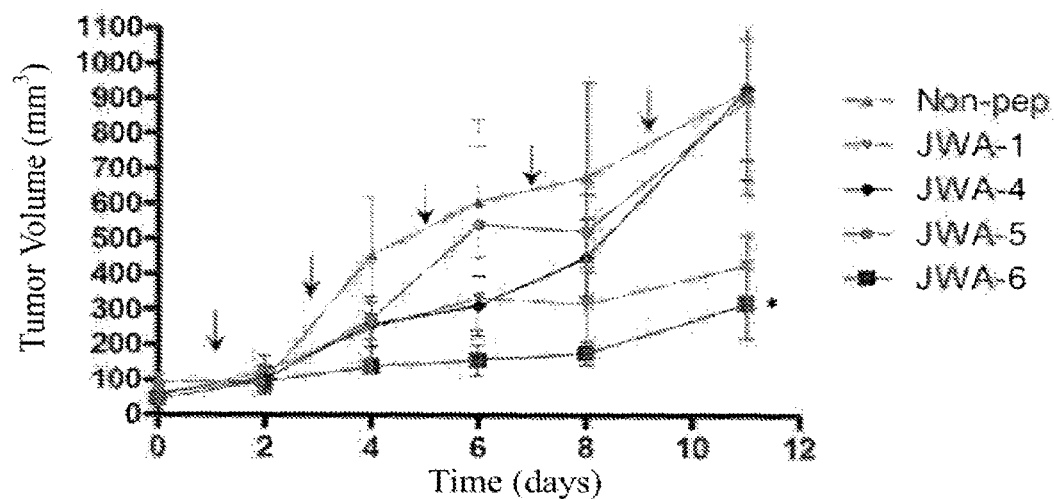
FIG. 11 is a graph of tumor volume changes in Example 4, wherein arrows denote drug administration times, and an asterisk * indicates P<0.05.
Figure 12:
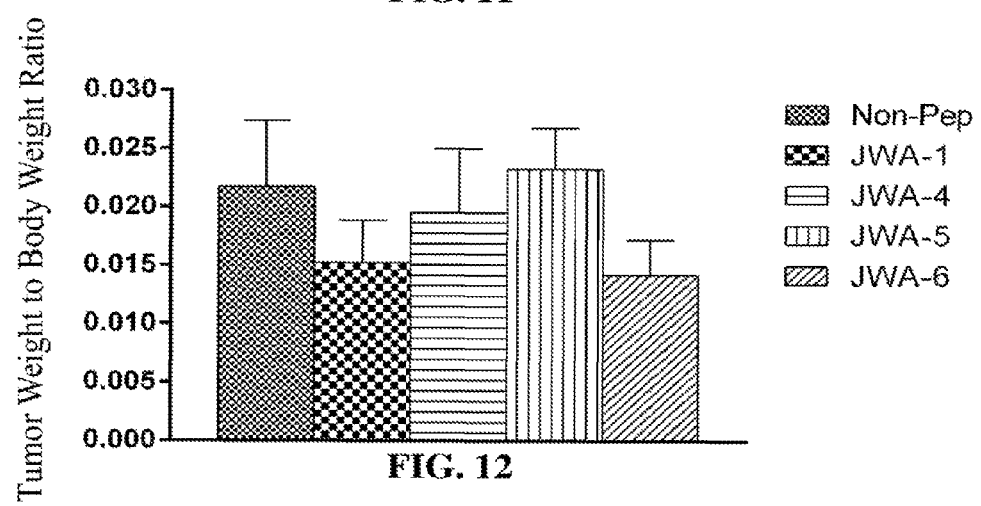
FIG. 12 is a tumor weight to body weight ratio graph of Example 4.
Figure 13:
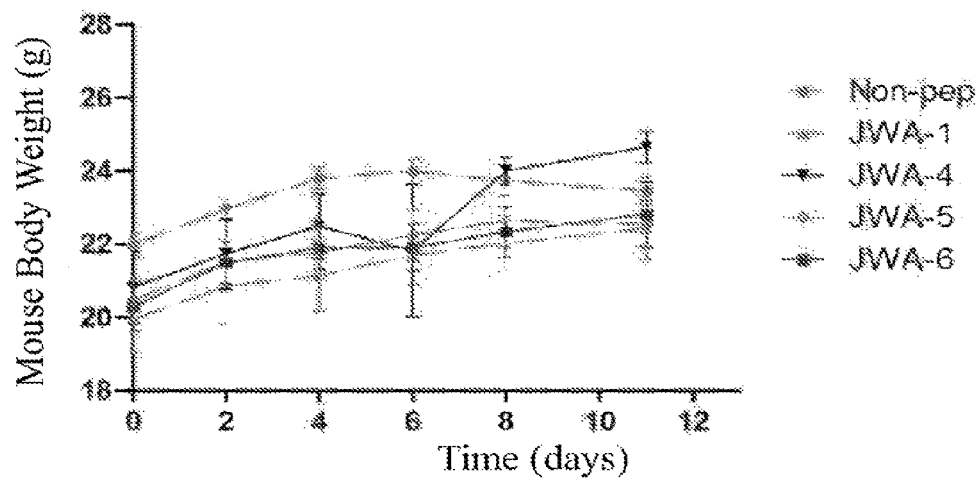
FIG. 13 is a graph of mouse body weight changes in Example 4.
Figure 14:
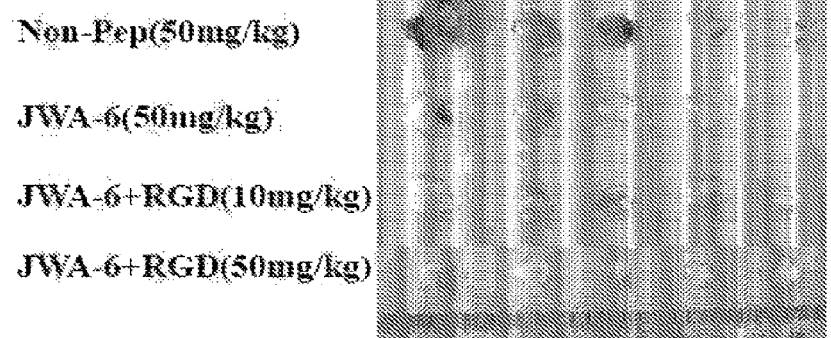
FIG. 14 is a tumor formation comparison among a non-pep group, a polypeptide JWA-6 (50 mg/kg) group, a polypeptide JWA-6+RGD (10 mg/kg) group, and a polypeptide JWA-6+RGD (50 mg/kg) group in Example 5.
Figure 15:
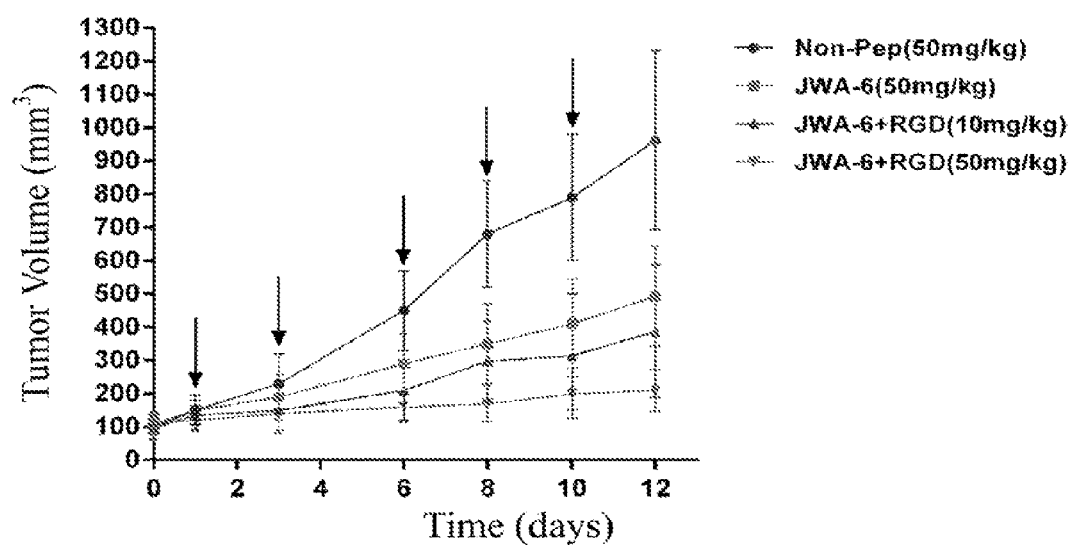
FIG. 15 is a graph of tumor volume changes in Example 5, wherein arrows denote drug administration times.
Figure 16:
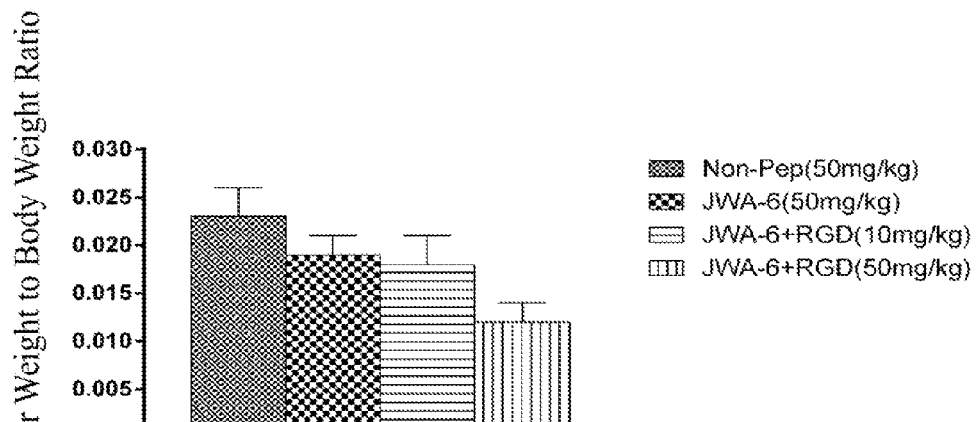
FIG. 16 is a tumor weight to body weight ratio graph of Example 5.
Figure 17:
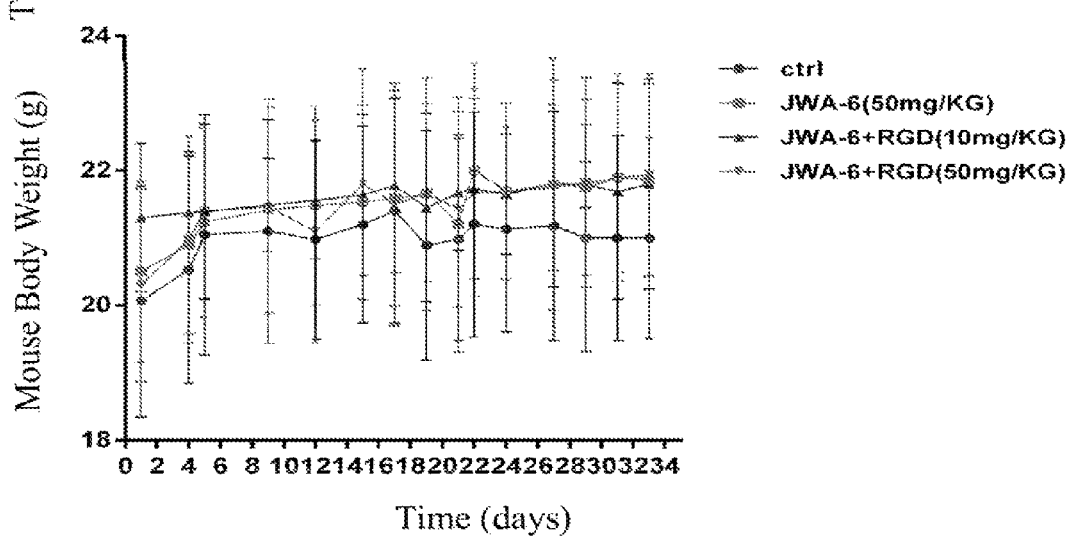
FIG. 17 is a graph of mouse body weight changes in Example 5.
Figure 18:
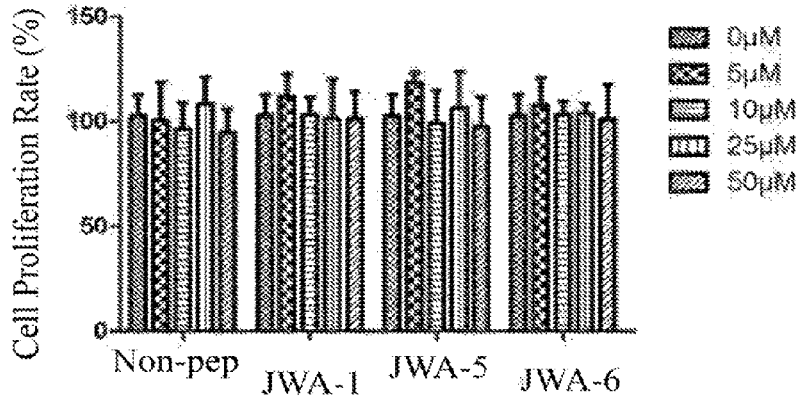
FIG. 18 is a graph showing results of impact of various polypeptides on A375 cells after 24 hrs in Example 6.
Figure 19:
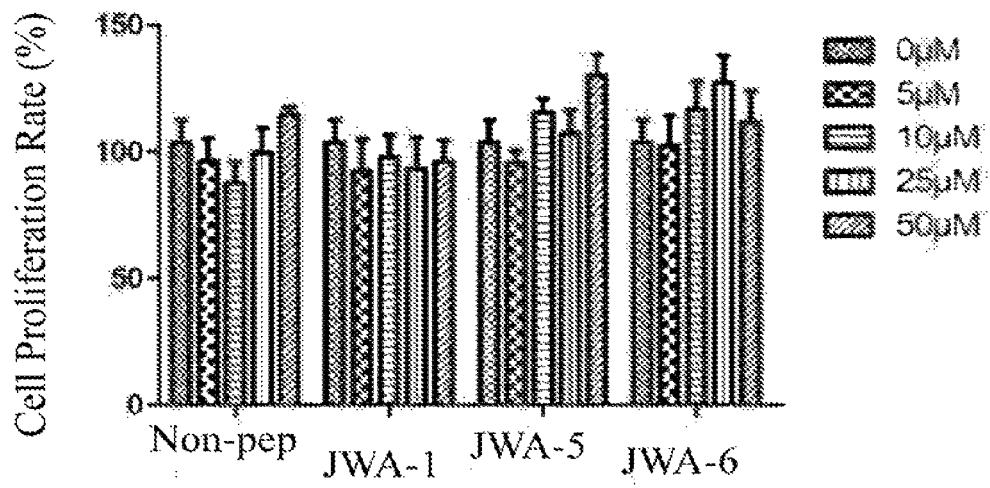
FIG. 19 is a graph showing results of impact of various polypeptides on A375 cells after 48 hrs in Example 6.
Figure 20:
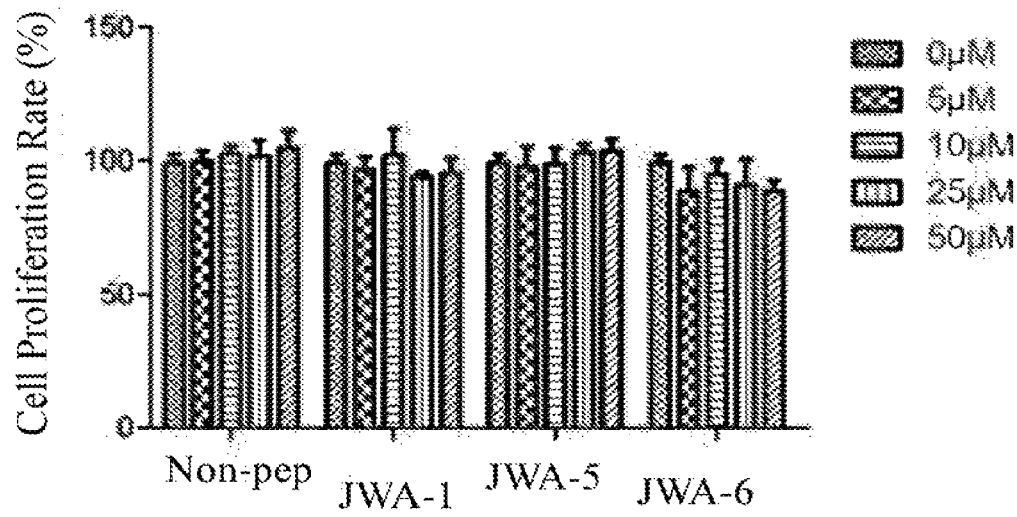
FIG. 20 is a graph showing results of impact of various polypeptides on A375 cells after 72 hrs in Example 6.
Figure 21:
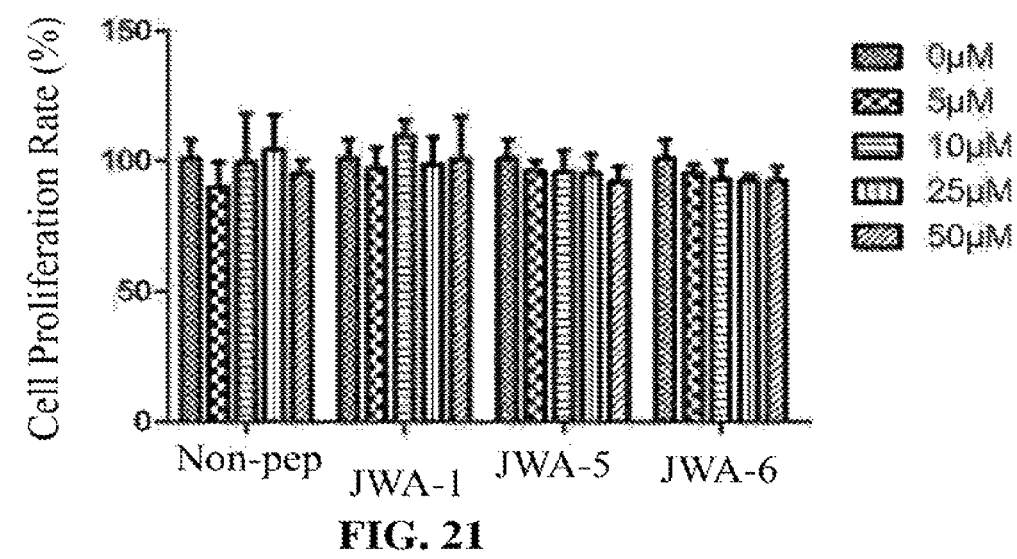
FIG. 21 is a graph showing results of impact of various polypeptides on B16 cells after 24 hrs in Example 6.
Figure 22:
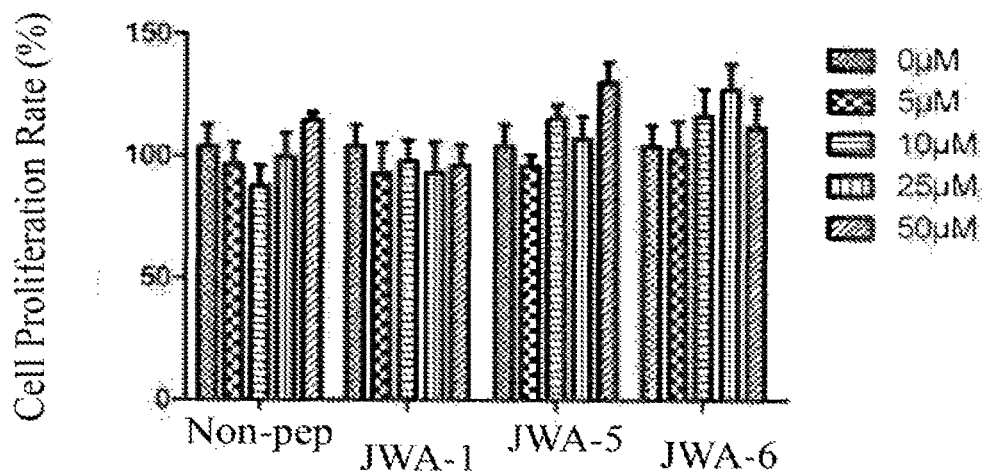
FIG. 22 is a graph showing results of impact of various polypeptides on B16 cells after 48 hrs in Example 6.
Figure 23:
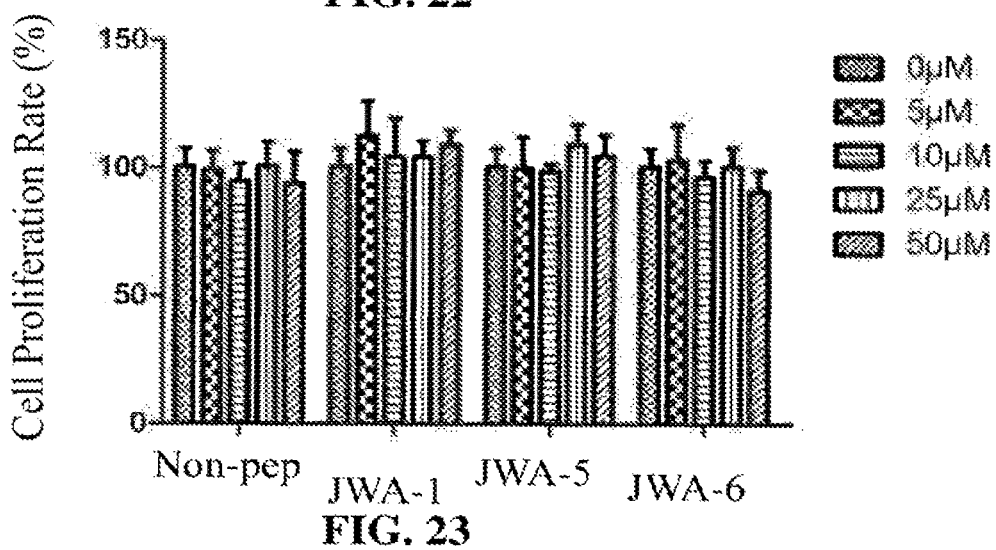
FIG. 23 is a graph showing results of impact of various polypeptides on B16 cells after 72 hrs in Example 6.

For further illustrating the invention, experiments detailing an anti-tumor polypeptide and a method for preparing an anti-tumor drug comprising the same are described below. It should be noted that the following examples are intended to describe and not to limit the invention.

The sequences of JWA protein (containing 188 amino acids) are as shown in FIG. 1. The inventors of this patent have designed a series of random polypeptide sequence fragments directed at portions of JWA protein outside the transmembrane domains and carried out synthesis using existing method (such as fluorenylmethyloxycarbonyl (Fmoc) method), and thereafter performed screening and identification. The following embodiments provide detailed descriptions of screening and identification processes, and besides active polypeptides some representative non-active polypeptides were selected, although it should not be construed that only these polypeptides were involved in the research process.

Example 1 Design and Synthesis of Polypeptides

The designed and synthesized polypeptides of this example are as shown in Table 1, wherein the amino acid sequences selected for JWA-1, JWA-2, and JWA-3 are consistent with the shaded portions in FIG. 1.

TABLE 1

Designed and synthesized polypeptide sequences of Example 1

| Name | Amino Acid Sequence (N-terminus - C-terminus) | Phosphorylation Site | SEQ ID NO: |
|---|---|---|---|
| JWA-1 | 6-aminocaproic acid-FFPGSDRFA | S phosphorylated | 1 |
| JWA-2 | 6-aminocaproic acid-FIHASLRLR | S phosphorylated | 2 |
| JWA-3 | 6-aminocaproic acid-LTDYISKV | Y phosphorylated | 3 |
| JWA-4 | 6-aminocaproic acid-GSD | S phosphorylated | -25 |
| JWA-5 | 6-aminocaproic acid-PGSDR | S phosphorylated | 4 |
| JWA-6 | 6-aminocaproic acid-FPGSDRF | S phosphorylated | 5 |

TABLE 1-continued

Designed and synthesized polypeptide sequences of Example 1

| Name | Amino Acid Sequence (N-terminus - C-terminus) | Phosphorylation Site | SEQ ID NO: |
|---|---|---|---|
| JWA-7 | 6-aminocaproic acid-FFPGSDRFA | Not phosphorylated | 6 |

During synthesis of the aforementioned polypeptide sequences, the N-terminus thereof may be acetylated and the C-terminus thereof amidated to prevent rapid degradation of the polypeptides.

Example 2 Selecting Polypeptides Having Anti-Tumor Activity from JWA-1, JWA-2, and JWA-3

Human melanoma A375 cells in the logarithmic phase of growth were cultured under sterile conditions to prepare a $5 \times 10^6/200$ µL cell suspension, and 200 µL cell suspension was separately injected into BALB/c nude mice subcutaneously. An electronic digital vernier caliper was used to measure the long-axis and short-axis diameters of the transplanted tumors, and the formula: Tumor Volume (TV)=½× Long-axis Diameter×Short-axis Diameter$^2$ was used to calculate the volume of the tumors. The mice were randomly grouped when the tumor volume reach about 100 mm$^3$.

Polypeptides JWA-1, JWA-2, JWA-3, and an equivalent peptide blend (Pep) of the three polypeptides were injected into the tumors of the various groups of mice respectively, and the doses used were 25 mg/kg and 10 mg/kg, respectively; the negative control group was injected with an equal amount of sterile phosphate-buffered saline (PBS). The polypeptide injection groups and the control group were administered on alternate days (48 hrs interval) by injection for 5 times; and the body weight of the mice and their tumor diameters were measured at each administration. After completion of the experiment the mice were sacrificed after anesthesia, tumors were separated from the bodies and their weight were measured.

The results were recorded as shown in FIGS. 2-5. In comparison with the control group (PBS group), the inhibition effect on subcutaneous tumor growth in nude mice in the 10 mg/kg polypeptide JWA-1 treated group was more significant, and the tumor weight to body weight ratio thereof was also smaller (P<0.05).

In addition, there was no statistical difference in average body weight of mice between the groups, and no drug toxicity reaction in the mice was observed during the experiment.

Melanoma is a highly malignant tumor, and the results of this example indicated that intratumoral injection of polypeptide JWA-1 in a dose of 10 mg/kg can significantly inhibit xenograft tumor growth of human melanoma A375 cells in nude mice.

Example 3 Selecting the Polypeptide JWA-1 Dose Having the Optimal Anti-Tumor Effect, and Probing the Impact of Polypeptide Phosphorylation on Anti-Tumor Effect The objective of this example was to ascertain the dose-effect relation between JWA polypeptides and tumor inhibition.

In this example, the method for dorsal subcutaneous tumor bearing of BALB/c nude mice by inoculation of A375 cells is the same as Example 2.

The aforementioned BALB/c nude mice inoculated with human melanoma A375 cells by intratumoral injection were separately treated using polypeptide JWA-1 of low dose (5 mg/kg), medium dose (10 mg/kg) and high dose (15 mg/kg); at the same time, a sterile PBS negative control group and a 10 mg/kg non-pep injection group (referred to simply as "non-pep group", the polypeptide sequence used was SEQ ID NO: 14; 6-aminoacetic acid-EEMQR, the N-terminus thereof being acetylated and the C-terminus thereof amidated) were established. The establishment of the non-pep group was for observing whether JWA polypeptides have any specific anti-tumor effect.

To verify the impact of phosphorylation of S in polypeptide JWA-1 on the anti-tumor effect thereof, a non-phosphorylated polypeptide JWA-7 injection group (10 mg/kg) was added in the aforementioned experiment.

The various groups were administered by intratumoral injection on alternate days for 5 times consecutively; and the body weight of the mice and their tumor diameters were measured at each administration. After completion of the experiment the mice were sacrificed after anesthesia, tumors were separated from the bodies and the tumor weights were measured.

The results were recorded as shown in FIGS. 6-9. The 10 mg/kg polypeptide injection group demonstrated significant tumor inhibition effect, and no trend of enhanced effect was detected along with dose increase, with the effect on the 5 mg/kg JWA-1 injection group similar to that on the 10 mg/kg group. Although the reason for non-dependence on dose has not been ascertained, the ability of JWA-1 to inhibit the growth of transplanted tumors in nude mice has been verified.

At the same time, the non-peptide (non-pep) group and the polypeptide JWA-7 injection group demonstrated no tumor inhibition effect. It can be known from the results of the polypeptide JWA-7 injection group that the phosphorylation of S in polypeptide JWA-1 is an imperative condition for its anti-tumor effect; hence it is not necessary to consider the effect of non-phosphorylated polypeptides.

In addition, there was no statistical difference in average body weight of mice between the groups, and no toxicity reaction in the mice was observed during the experiment.

Example 4 Selecting the Shortest Functional Unit of Polypeptide JWA-1

The objective of this example was to explore whether polypeptide JWA-1 still has anti-tumor effect after its length reduction.

To this end, polypeptides JWA-4, JWA-5, and JWA-6 were used in this example, and these polypeptides are based on polypeptide JWA-1 with 3, 2, or 1 amino acid(s) reduced from the N-terminus and C-terminus respectively.

In this example, the method for dorsal subcutaneous tumor bearing of BALB/c nude mice by inoculation of A375 cells is the same as Example 2.

The BALB/c nude mice inoculated with human melanoma A375 cells were separately treated using 10 mg/kg polypeptides JWA-1, JWA-4, JWA-5, and JWA-6; at the same time, a 10 mg/kg non-pep injection group (referred to simply as "non-pep group", the polypeptide sequence used was the same as Example 3) was established.

The various groups were administered by intratumoral injection on alternate days for 5 times consecutively; and the body weight of the mice and their tumor diameters were measured at each administration. After completion of the experiment the mice were sacrificed after anesthesia, tumors were separated from the bodies and the tumor weights were measured.

The results were recorded as shown in FIGS. 10-13. The tumor inhibition effect of polypeptide JWA-6 demonstrated similar and even better than that of polypeptide JWA-1, whereas the tumor inhibition effect of polypeptides JWA-4 and JWA-5 demonstrated significantly worse than that of polypeptide JWA-6. It can therefore be known from the results that polypeptide JWA-6 is the shortest functional unit of polypeptide JWA-1.

In addition, there was no statistical difference in average body weight of mice between the groups, and no toxicity reaction in the mice was observed during the experiment.

Example 5 Selecting a Functional Polypeptide Having Polypeptide JWA-6 as the Active Site and Specifically Targeting Integrin $\alpha v \beta_3$ The tumor inhibition effects of JWA functional polypeptides observed in Examples 2-4 were all results of direct intratumoral injection of the polypeptides. Taking into consideration that direct intratumoral injection can be difficult for clinical application, intraperitoneal injection was used to observe whether the JWA functional polypeptide still has good anti-tumor effect.

It can be known from prior art that the expression of integrin $\alpha_v\beta_3$ is increased on the cell surfaces of many malignant tumors (including melanoma), and that arginine-glycine-aspartic acid (RGD) sequence can specifically target integrin $\alpha_v\beta_3$. Therefore, this example is to explore the inhibition effect of polypeptide JWA-6 with an arginine-glycine-aspartic acid (RGD) sequence injected into the melanoma-bearing mice intraperitoneally.

The polypeptide designed and synthesized in this example was JWA-6+RGD whose sequence was SEQ ID NO: 7, i.e. 6-aminocaproic acid-FPGSDRF-GGGG-RGD, wherein amino acid S was phosphorylated. In addition, the N-terminus of the polypeptide sequence was acetylated and the C-terminus thereof was amidated during synthesis to prevent rapid degradation of the polypeptide. In this example, non-obese diabetic/severe combined immunodeficiency (NOD/SCID) mice were chosen for tumor-bearing model and the method for dorsal subcutaneous tumor bearing by inoculation of human melanoma A375 cells is the same as Example 2. The mice were randomly divided into four treatment groups after the tumors grew to a volume of about 100 mm$^3$.

Taking into consideration the polypeptide dose reaching the tumors partially after intratumoral injection, on the basis of the 10 mg/kg polypeptide used in the preceding example, a 50 mg/kg polypeptide group was added in this example, a single JWA-6 polypeptide at a dose of 50 mg/kg was used as a control group for reviewing the targeted anti-tumor effect, and a 50 mg/kg non-pep group was used to compare the specific anti-tumor effect of the JWA functional polypeptide.

Then, 50 mg/kg polypeptide JWA-6, 10 mg/kg polypeptide JWA-6+RGD, 50 mg/kg polypeptide JWA-6+RGD, and 50 mg/kg non-pep (the polypeptide sequence used was the same as Example 3) were injected intraperitoneally. The various groups were administered with injection on alternate days for 5 times consecutively; and the body weight of the mice and their tumor diameters were measured at each administration. After completion of the experiment the mice were sacrificed after anesthesia, tumors were separated from the bodies and the tumor weights measured.

The results were recorded as shown in FIGS. 14-17. When administered by intraperitoneal injection, the 50 mg/kg polypeptide JWA-6 and 10 mg/kg polypeptide JWA-6+RGD both demonstrated a certain degree of tumor inhibition effect, while the 50 mg/kg polypeptide JWA-6+RGD demonstrated better tumor inhibition effect.

In addition, there was no statistical difference in average body weight of mice between the groups, and no toxicity reaction to these three polypeptides in the mice was observed during the experiment.

In this example, 4 G (glycine) molecules were added between JWA-6 and RGD sequence, the purpose of which was to allow the JWA-6 polypeptides having anti-tumor activity to have a free space after the binding of RGD to integrin $\alpha_v\beta_3$ on the tumor cell surfaces, thus enhancing the its biological effects. The inventors of the invention discovered through research that the number of G (glycine) molecules inserted between JWA-6 and RGD sequence can vary and may be greater than or equal to zero, but preferably smaller than or equal to ten.

Firstly, the following polypeptides containing RGD sequence were designed and synthesized (see Table 2).

TABLE 2

| Polypeptides containing RGD sequence | | | |
|---|---|---|---|
| Name | Amino Acid Sequence (N-terminus - C-terminus) | Phosphorylation Site | SEQ ID NO: |
| JWA-6 + RGD0 | 6-aminocaproic acid-FPGSDRF-RGD | S phosphorylated | 26 |
| JWA-6 + RGD1 | 6-aminocaproic acid-FPGSDRF-G-RGD | S phosphorylated | 27 |
| JWA-6 + RGD3 | 6-aminocaproic acid-FPGSDRF-GGG-RGD | S phosphorylated | 28 |
| JWA-6 + RGD7 | 6-aminocaproic acid-FPGSDRF-(G)$_7$-RGD | S phosphorylated | 29 |
| JWA-6 + RGD10 | 6-aminocaproic acid-FPGSDRF-(G)$_{10}$-RGD | S phosphorylated | 30 |

During synthesis of the aforementioned polypeptide sequences, the N-terminus thereof may be acetylated and the C-terminus thereof may be amidated to prevent rapid degradation of the polypeptides.

Thereafter, the tumor bearing mice were obtained using the foregoing method of this example and divided into seven injection groups which were intraperitoneally injected with polypeptides JWA-6+RGD, JWA-6+RGD0, JWA-6+RGD1, JWA-6+RGD3, JWA-6+RGD7, JWA-6+RGD10, and non-pep (the polypeptide sequence used was the same as Example 3) at a dose of 50 mg/kg. The various groups were administered by intraperitoneal injection on alternate days for 5 times consecutively; and the body weight of the mice and their tumor diameters were measured at each administration. The day of first administration was taken as the first day, and the experiment was stopped on the twelfth day when the mice were sacrificed after anesthesia, and tumors were separated from the bodies and the tumor weights were measured.

Because of space constraints, the actual experimental data is not listed herein. The experimental data indicated that the anti-tumor activity of the polypeptides will not be affected when the number of glycine molecules between RGD sequence and JWA-6 is in the range of 0-10.

Example 6 In Vitro Effects of Polypeptides JWA-1, JWA-5, and JWA-6 on the Activity of Human Melanoma A375 Cells and Mouse Melanoma B16F10 Cells The objective of this example was to explore the in vitro effects of JWA functional polypeptides on the activity of melanoma cells.

B16F10 or A375 cells in the logarithmic phase of growth were trypsinized and seeded in a 96-well plate ($5\times10^3$ cells/well), and were treated with different doses (0 μM, 5 μM, 10 μM, 25 μM, 50 μM) of polypeptide JWA-1, JWA-5, JWA-6 or non-pep (the polypeptide sequence used was the same as Example 3) for 24 hrs, 48 hrs and 72 hrs, respectively. The original culture medium was removed from the 96 wells at the indicated time and cell proliferation was determined with CCK8 reagent according to the manufacturer's instructions. Four duplicate samples were taken from each group and the experiments were repeated for three times.

The results were recorded as shown in FIGS. 18-23. In comparison with the control group, no inhibition effect on A375 cells and B16F10 cells was found upon polypeptides JWA-1, JWA-5, and JWA-6 treatment in vitro.

Example 7 Combined Effect of Polypeptides JWA-1, JWA-6, and $As_2O_3$ (ATO) on Apoptosis of Human Melanoma A375 Cells The results of Example 6 indicated that treatment of human melanoma A375 cells with JWA functional polypeptides alone generated no cytotoxicity Taking into consideration that in vivo experiments are far more complex than in vitro experiments, JWA functional polypeptides might promote the apoptosis effect of chemotherapy drugs. The inventors of the invention have discovered that JWA gene plays an important role in regulating ATO induced apoptosis, and overexpression JWA gene significantly enhances ATO-induced tumor apoptosis. Therefore, the objective of this example was to determine whether the combined use of JWA functional polypeptides and ATO can enhance ATO induced apoptosis of melanoma cells.

Figure 24:
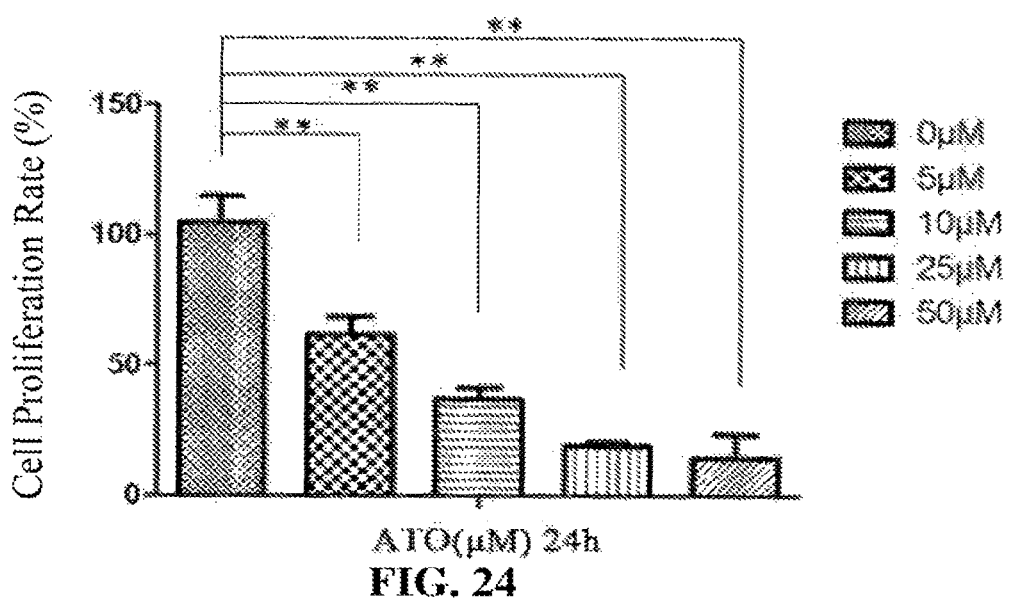
FIG. 24 is a graph showing results of cell treatment using solely arsenic trioxide (ATO) after 24 hrs in Example 7, wherein asterisks ** indicate P<0.01.
Figure 25:
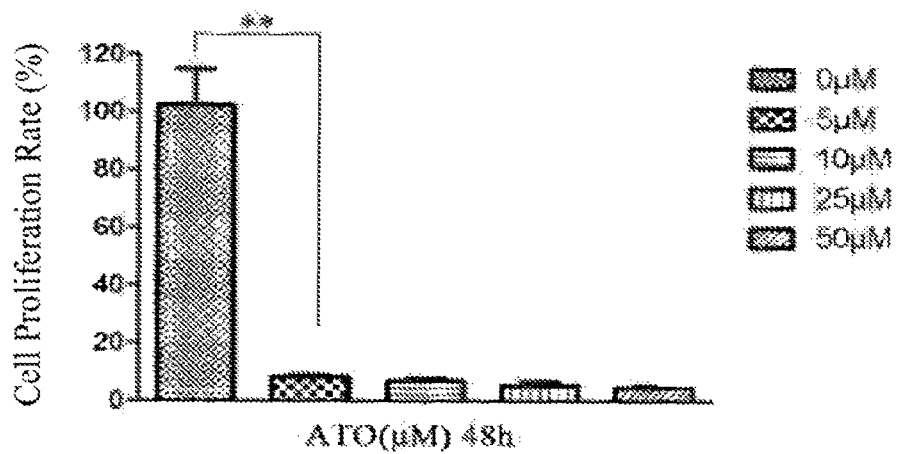
FIG. 25 is a graph showing results of cell treatment using solely arsenic trioxide (ATO) after 48 hrs in Example 7, wherein asterisks ** indicate P<0.01.
Figure 26:
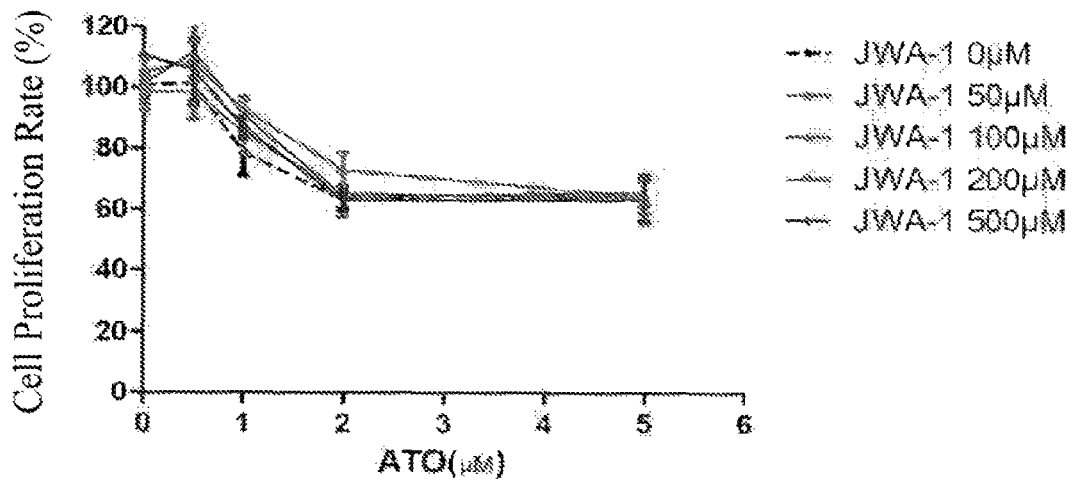
FIG. 26 is a graph showing results of combined impact of arsenic trioxide (ATO) (0.5 µM, 1 µM, 2 µM, 5 µM) and polypeptide JWA-1 on A375 cells after 24 hrs in Example 7.
Figure 27:
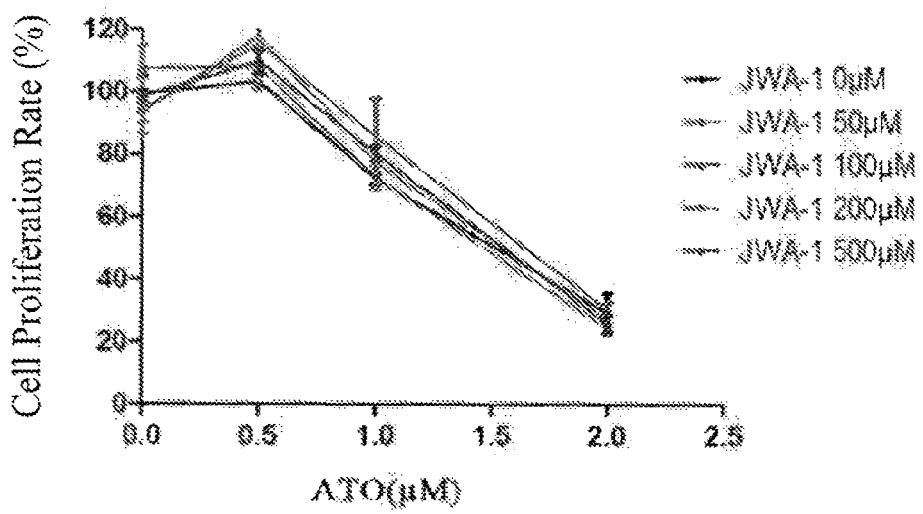
FIG. 27 is a graph showing results of combined impact of arsenic trioxide (ATO) (0.5 µM, 1 µM, 2 µM) and polypeptide JWA-1 on A375 cells after 48 hrs in Example 7.

Firstly, the dose and time for treatment of A375 cells with ATO were determined. A375 cells in the logarithmic phase of growth were conventionally digested and seeded in a 96-well plate ($5\times10^3$ cells/well), and different doses (5 μM, 10 μM, 25 μM, 50 μM) of ATO were used to treat the cells for 24 hrs and 48 hrs after cell attachment. It was discovered that the activity of A375 cells was reduced by 40% after 24 hrs of treatment with 5 μM ATO (as shown in FIG. 24), and that the cell growth inhibition rate was approximately 100% after 48 hrs of treatment with different doses of ATO (as shown in FIG. 25). Therefore, ATO with a concentration smaller than or equal to 5 μM was chosen to treat the cells for 24 hrs for subsequent reference of dose and time for combined medication.

Figure 28:
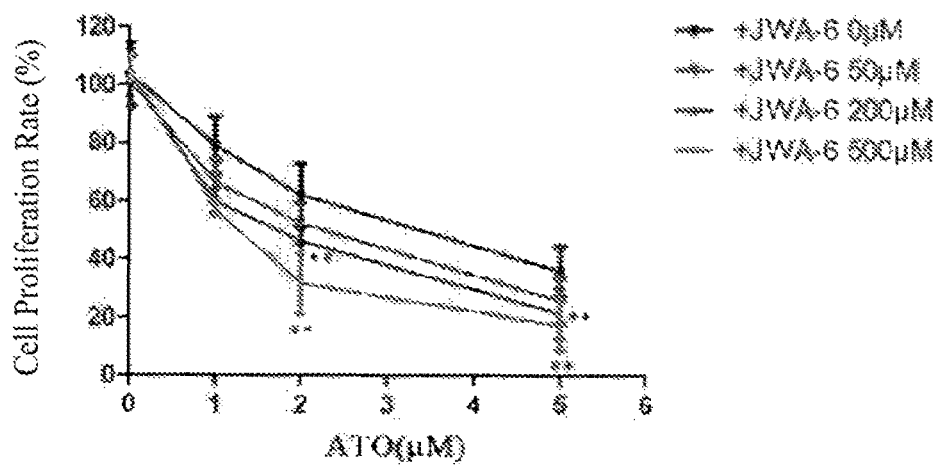
FIG. 28 is a graph showing results of combined impact of arsenic trioxide (ATO) (1 µM, 2 µM, 5 µM) and polypeptide JWA-6 on A375 cells after 24 hrs in Example 7.
Figure 29:
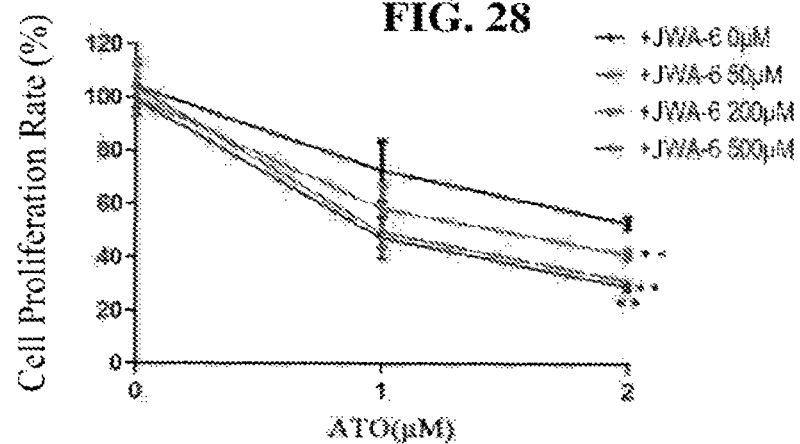
FIG. 29 is a graph showing results of combined impact of arsenic trioxide (ATO) (1 µM, 2 µM) and polypeptide JWA-6 on A375 cells after 48 hrs in Example 7.

After determining the time and dose of ATO acting on the cells, polypeptides JWA-1 and JWA-6 at a dose of 50 μM, 100 μM, 200 μM and 500 μM respectively were used in combination with ATO at a dose of 0.5 μM, 1 μM, 2 μM and 5 μM to treat A375 cells for 24 hrs and 48 hrs respectively, after which the cytoactivity was examined and JWA-1 was found to have no synergistic effect with ATO while the combined used of JWA-6 and ATO exerts obvious toxicity to A375 cells (as shown in FIGS. 28-29).

The combined effect of ATO and polypeptide JWA-6 on the self-destruction of protein expression was also determined A375 cells in the logarithmic phase of growth were conventionally digested and $5\times10^5$ cells were inoculated evenly in a 60 mm cell culture dish, and different doses of ATO were used to individually treat the cells for 24 hrs, or different doses of ATO in combination with different doses of polypeptide JWA-6 were used to treat the cells for 24 hrs, after which 0.18 mL of RIPA lysis buffer containing 0.5% phenylmethanesulfonyl fluoride (PMSF) was added to extract protein. After centrifugation at 12000×g for 15 minutes, the supernatant was taken, protein concentration was examined. Based on the molecular weight measured, a polyacrylamide gel having a suitable concentration was chosen for protein electrophoresis where each well was added with 70 ng of protein, and the conditions for electrolysis were 60 V, 30 minutes and 90 V, 1-1.5 hrs. After completion of the electrolysis, semi-dry transfer was performed to transfer the protein from the gel onto a polyvinylidene difluoride (PVDF) membrane. After completion of the transfer, the membrane was blocked with 5% skim milk at room temperature for 1-2 hrs. Then, the membrane was washed 3 times (each lasting 5 minutes) using Tris-buffered Saline with Tween (TBST) containing 0.1% Tween-20, and incubation of the corresponding antibody was performed overnight at 4° C. On the next day, membrane was washed 3 times (each lasting 5 minutes) using Tris-buffered Saline with Tween (TBST) containing 0.1% Tween-20; incubation of secondary antibody was performed at room temperature for 1-2 hrs; and again membrane was washed 8 times (each lasting 5 minutes) using Tris-buffered Saline with Tween (TBST) containing 0.1% Tween-20. The membrane was added with enhanced chemiluminescence (ECL) liquid and exposed.

Figure 30:
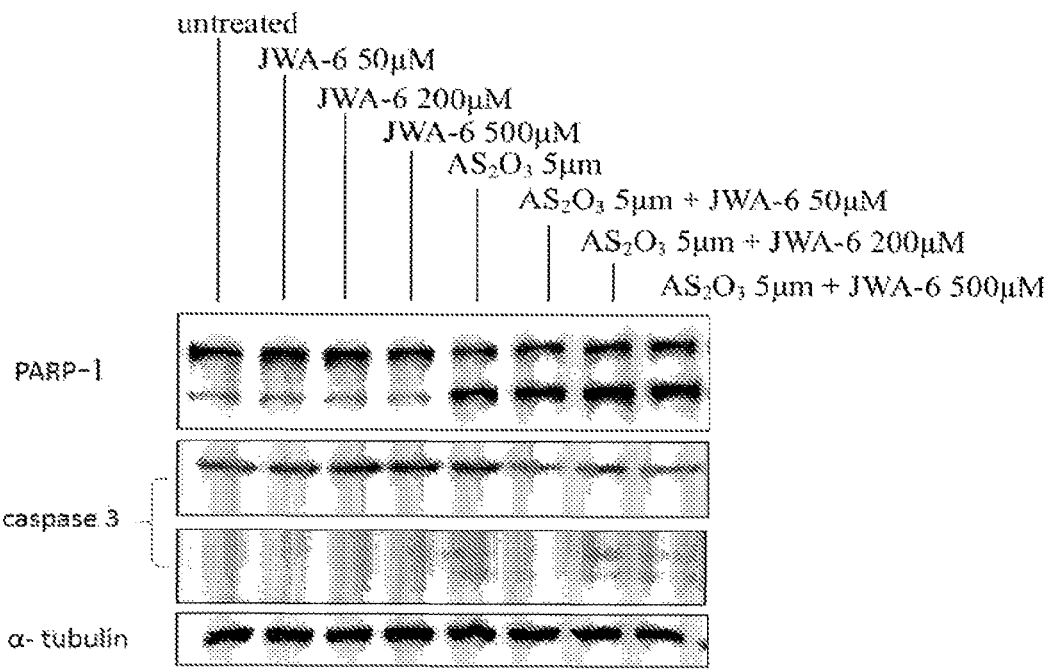
FIG. 30 illustrates a Western Blot assay showing the expression of PARP-1 and caspase3 after treatment of A375 cells using solely polypeptide JWA-6 for 24 hrs and after treatment of A375 cells using polypeptide JWA-6 in combination with arsenic trioxide (ATO) for 24 hrs, respectively, in Example 7, wherein α-tubulin is an endogenous reference protein.
Figure 31:
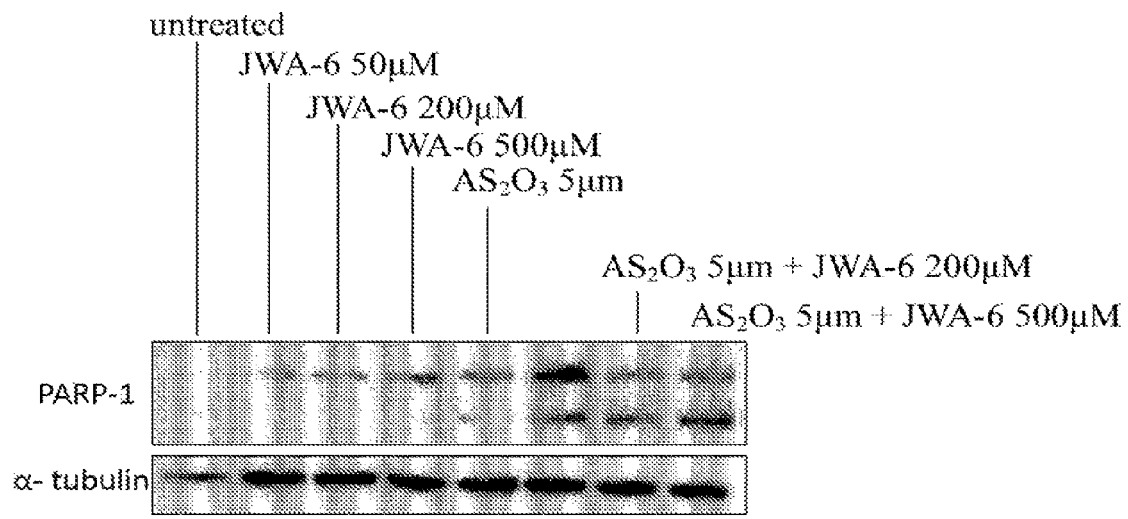
FIG. 31 illustrates a Western Blot assay showing changes in the expression of PARP-1 after treatment of B16 cells using solely polypeptide JWA-6 for 24 hrs and after treatment of B16 cells using polypeptide JWA-6 in combination with arsenic trioxide (ATO) for 24 hrs, respectively, in Example 7, wherein α-tubulin is an endogenous reference protein.

Through Western Blot experiment, it was discovered that compared to the untreated group and the group using ATO alone, cleaved caspase-3 and cleaved PARP-1 in the combined medication group of ATO and polypeptide JWA-6 were significantly increased, which indicated that the combined action of ATO and polypeptide JWA-6 further activated the mechanism of apoptosis to accelerate the apoptosis of A375 cells (as shown in FIG. 30). In addition, changes of PARP-1 were also seen in B16 cells (as shown in FIG. 31).

Example 8 Selecting Cell-Penetrating Peptides (CPPs) Capable of Bringing JWA Functional Polypeptides into Cells To enable JWA functional polypeptides to effectively penetrate into tumor cells, four typical CPPs: R9, TAT, pep-1, 2K (see Table 3), and a blank control having only JWA-1 were selected, the cell-penetrating peptide (CPP) with the highest cell-penetrating effect, its optimal action concentration and optimal action time were selected from the cell model.

TABLE 3

Cell-penetrating peptide (CPP) sequences

| Name | Amino Acid Sequence (N-terminus-C-terminus) | SEQ ID NO: |
|------|---------------------------------------------|------------|
| R9   | 6-aminocaproic acid-RRRRRRRRR               | 8          |
| TAT  | 6-aminocaproic acid-RKKRRQRRR               | 9          |
| pep-1| 6-aminocaproic acid-KETWWETWWTEWSQPKKKRKV   | 10         |
| 2K   | 6-aminocaproic acid-YGRKKRRQRRR             | 11         |

Figure 32:
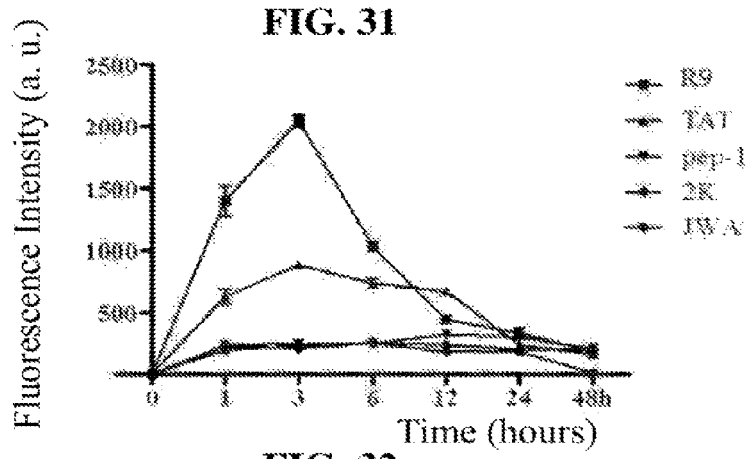
FIG. 32 is a graph of fluorescence intensity versus time after the entry of various cell-penetrating peptide (CPP) sequences and JWA-6 sequence with a concentration of 10 µM into SGC7901 cells in Example 8.
Figure 33:
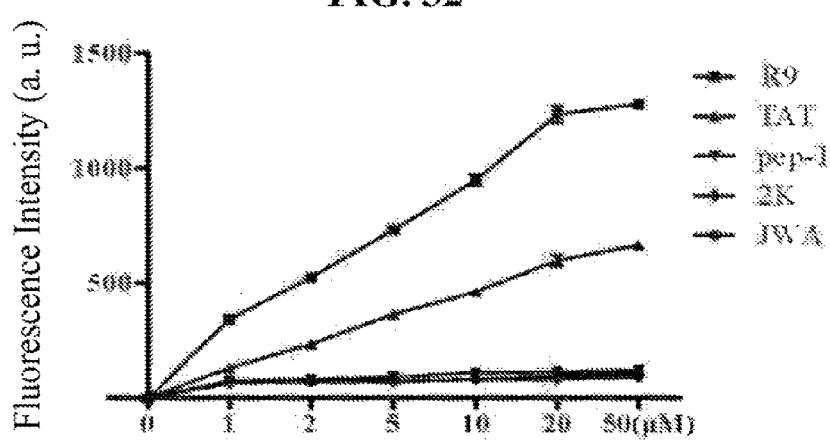
FIG. 33 is a fluorescence intensity comparison between various cell-penetrating peptide (CPP) sequences and JWA-6 sequence in different doses after their effects on SGC7901 cells for 3 hrs and their entry thereinto in Example 8.
Figure 34:
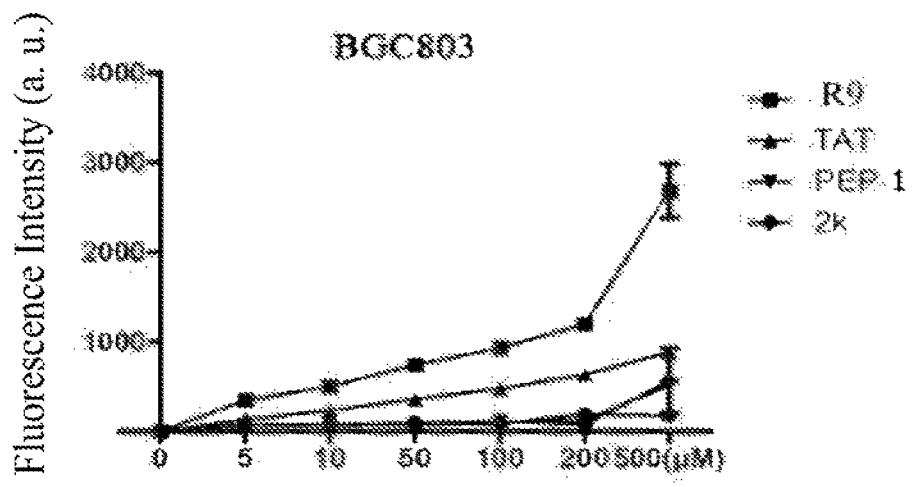
FIG. 34 is a fluorescence intensity comparison between various cell-penetrating peptide (CPP) sequences in different doses after their effects on BGC803 cells for 3 hrs and their entry thereinto in Example 8.
Figure 35:
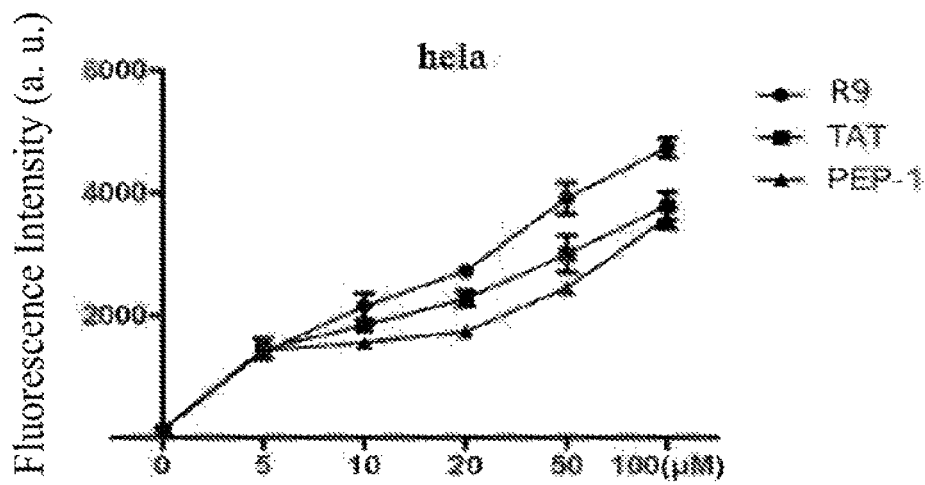
FIG. 35 is a fluorescence intensity comparison between various cell-penetrating peptide (CPP) sequences in different doses after their effects on HeLa cells for 3 hrs and their entry thereinto in Example 8.
Figure 36:
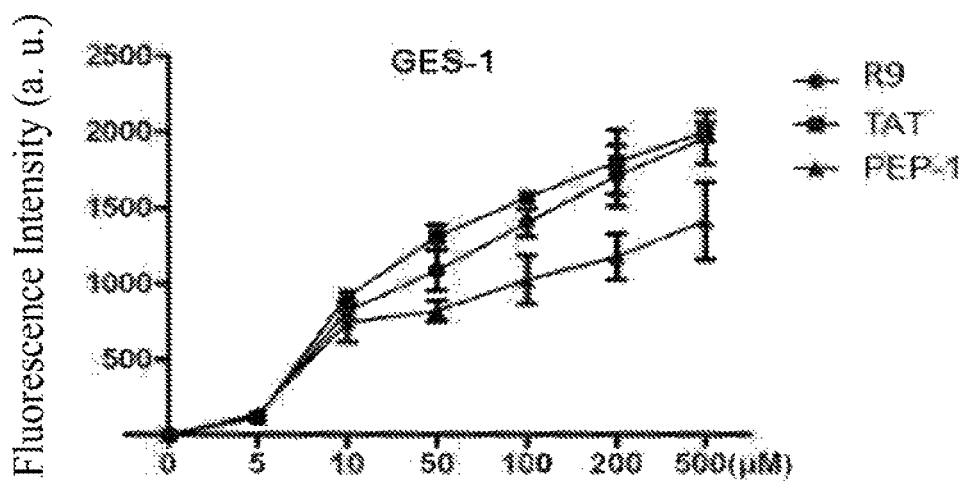
FIG. 36 is a fluorescence intensity comparison between various cell-penetrating peptide (CPP) sequences in different doses after their effects on GES-1 cells for 3 hrs and their entry thereinto in Example 8.

The fluorescence was at the highest level when cell-penetrating peptides (CPPs) were found to have entered the cells for 3 hrs on SGC7901 gastric cancer cell; and when the concentration was 20 μM the fluorescence was balanced, and the differences between R9 group and other groups were the most significant (as shown in FIGS. 32-33). In addition, the same effects were proven in BGC803 cells, HeLa cells and normal gastric epithelial cells GES-1 (as shown in FIGS. 34-36).

Therefore, R9 having a relatively better effect was chosen in subsequent experiments as the cell-penetrating peptide (CPP) bringing JWA functional polypeptides into cells to exert their biological function.

To facilitate the use of fluorescence microscopy to directly observe whether polypeptides have the ability to enter cells, the N-terminuses of the aforementioned sequences and JWA-1 were modified with fluorescein isothiocyanate (FITC) and the C-terminuses thereof were amidated.

Example 9 Combined Effect of JWA Functional Polypeptides Having Cell-Penetrating Peptide (CPP) Sequences and As$_2$O$_3$ (ATO) on Tumor Apoptosis The objective of this example was to explore whether JWA functional polypeptides having CPP sequences can directly induce tumor apoptosis or enhance drug-induced tumor apoptosis.

Six groups with different treatment methods directed against SGC7901 cells were designed: blank control group; transfection Flag-control group; transfection Hag-JWA group; transfection Flag-JWA and ATO combined treatment group; ATO treatment group; and polypeptide CPP-1 and ATO combined treatment group. After 24 hrs of treatment for each group, Annexin V-PE/PI flow cytometry was used to examine apoptosis and Western Blot was used to detect the level of PARP-1.

Flag-JWA was recombinant expression plasmid with JWA gene; Flag-control was used as blank plasmid control; the sequence of polypeptide CPP-1 was SEQ ID NO: 12, i.e. 6-aminocaproic acid-(R)$_9$-FFPGSDRFA, and the amino acid S was phosphorylated.

Cell transfection group: liposome mediated transfection (Lipofectamine™ 2000 Transfection Kit) was used. SGC7901 cells were trypsinized, diluted with antibiotic-free DMEM medium containing 10% fetal bovine serum (FBS), rapidly homogenized and added into a 6-well plate; transfection was performed within 24 hrs at a dose of 4 μg/well for Flag-control and 4 μg/well for Flag-JWA 4 μg/well; 250 μL of preheated serum-free and antibiotic-free DMEM medium was added; liposome was added to the 250 μL of serum-free and antibiotic-free DMEM medium at a ratio of 10 μL/well; after incubation at room temperature for 5 minutes, the two tubes were thoroughly mixed and placed at room temperature for 20 minutes, during which the culture medium in the dish was removed and replaced with 2 mL of serum-supplemented antibiotic-free DMEM medium. 500 μL of the mixture was added into various dishes, and the serum-supplemented antibiotic-free DMEM medium was replaced after 5 hrs to continue the cultivation for 24 hrs.

Transfection plasmid plus ATO treatment group: the method of transfection was the same as mentioned above. The serum-supplemented antibiotic-free DMEM medium containing 5 μM ATO was replaced after 5 hrs to continue the cultivation for 24 hrs.

Polypeptide CPP-1 plus ATO treatment group: SGC7901 cells were trypsinized, diluted with a DMEM complete culture medium, rapidly homogenized and added into 35 mm dishes; the trypsinized cell culture was placed in a 5% CO$_2$ incubator for incubation at a temperature of 37° C. to reach a degree of polymerization of 80%. 20 μM polypeptide JWA-1-CPP working medium and 5 μM ATO working medium were prepared. Polypeptide CPP-1 was first used to treat the cells for 3 hrs, and it was replaced with ATO working medium to treat the cells for 24 hrs.

In normal cells, phosphatidyl serine (PS) are distributed on the inside of cell membrane lipid bilayer, and at the early stage of apoptosis the phosphatidyl serine (PS) in cell membranes is turned over from the inside of lipid membrane to the outside thereof. Annexin V is a Ca$^{2+}$-dependent phospholipids-binding protein with a molecular weight of between 35 and 36 kD and a high affinity for phosphatidyl serine (PS), therefore it can be bound with membranes of cells at early stage of apoptosis through phosphatidyl serine (PS) with exposed cellular laterals. Annexin V was labeled with fluorescein phycoerythrin (PE); fluorescence microscopy or flow cytometry could be employed to examine apoptosis with the labeled Annexin V used as a fluorescent probe. 7-AAD (7-amino-actinomycin D) is a nucleic acid dye that cannot pass through normal plasmalemmas. Along with the progress of cell apoptosis, the permeability of plasmalemmas to 7-AAD is gradually increased and coupled with the controlled degradation of DNA during apoptosis, 7-AAD can emit bright red fluorescence under excitation by excitation light with suitable wavelength. Cells were divided into three group by the fluorescence intensity of 7-AAD labeling DNA: strong fluorescence of 7-AAD indicates dead cells, weak fluorescence of 7-AAD indicates apoptotic cells, and undetectable fluorescence of 7-AAD indicates normal active cells.

Figure 37:
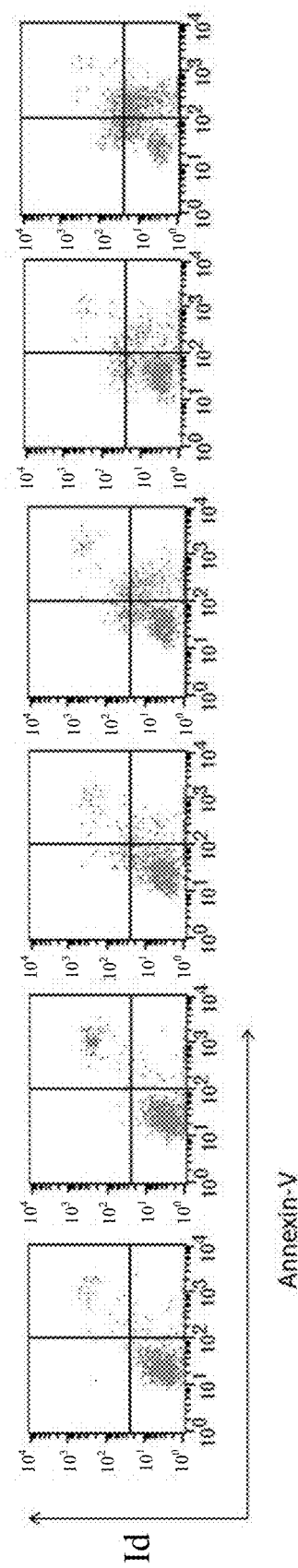
FIG. 37 is a graph showing results of apoptosis detected by flow cytometry in Example 9.
Figure 38:
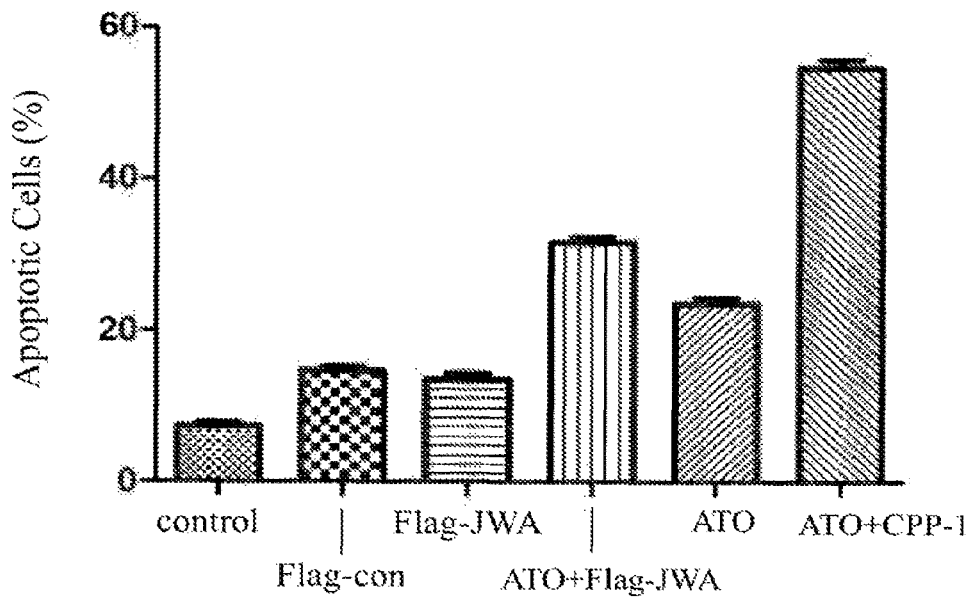
FIG. 38 is a statistical histogram corresponding to FIG. 7.

After treatment of the various treatment groups, the cells were trypsinized to prepare a cell suspension, Annexin V-PE/7-AAD staining was performed, and flow cytometry was used to examine apoptosis; the results were recorded as shown in FIG. 37. The foregoing results were plotted using Graphpad prism 5 to obtain a histogram (as shown in FIG. 38). The results indicated that: there was no statistical difference in apoptosis rate between the transfection Flag-JWA group and the transfection Flag-control group; the apoptosis rate of the polypeptide CPP-1 and ATO combined action group was the highest at 55.76%, which was higher than that of the transfection Flag-JWA and ATO combined action group (32.87%) and higher than that of the pure ATO treatment group (24.69%).

Figure 39:
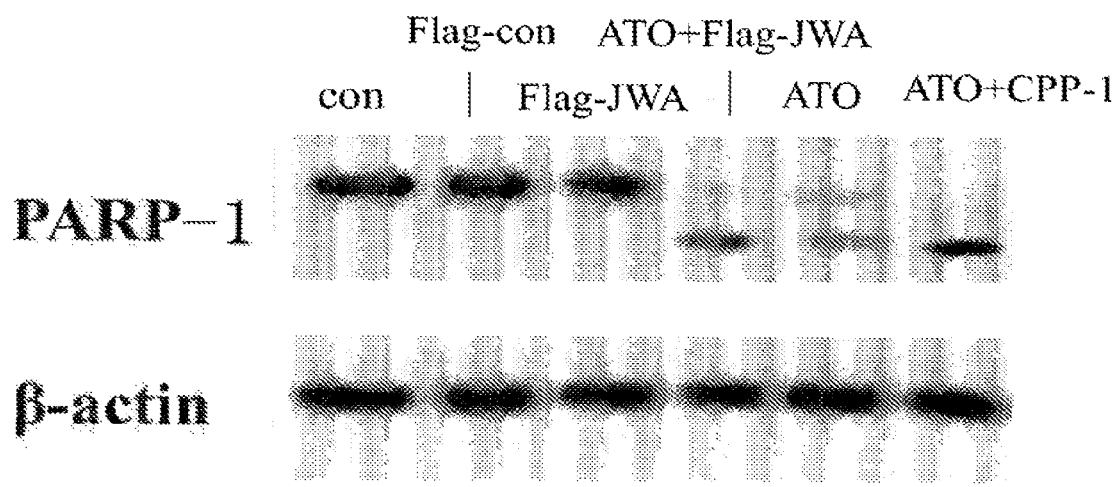
FIG. 39 illustrates a Western Blot assay showing resultant expression levels of PARP-1 in Example 9.

SGC7901 cells were treated using the foregoing treatment method of this example, and experiment was conducted using the Western Blot method of Example 7. The results of Western Blot experiment indicated that the expression of PARP-1 spliceosome in the polypeptide CPP-1 and ATO combined action group was higher than those of other groups (as shown in FIG. 39), which suggested that the apoptosis rate of that group was the highest and the results were consistent with the results of Annexin V-PE/7-AAD flow cytometry. The results demonstrated that polypeptide CPP-1 can accelerate ATO-induced tumor apoptosis.

Thereafter, the inventors of this patent continued to conduct research on the effects of singly using polypeptide CPP-JWA-6 and using polypeptide CPP-JWA-6 in combination with ATO for treatment of A375 cells and SGC7901 cells on the apoptosis thereof. The sequence of polypeptide CPP-JWA-6 was SEQ ID NO: 13, i.e. 6-aminocaproic acid-(R)$_9$—FPGSDRF, and the amino acid S was phosphorylated.

Figure 40:
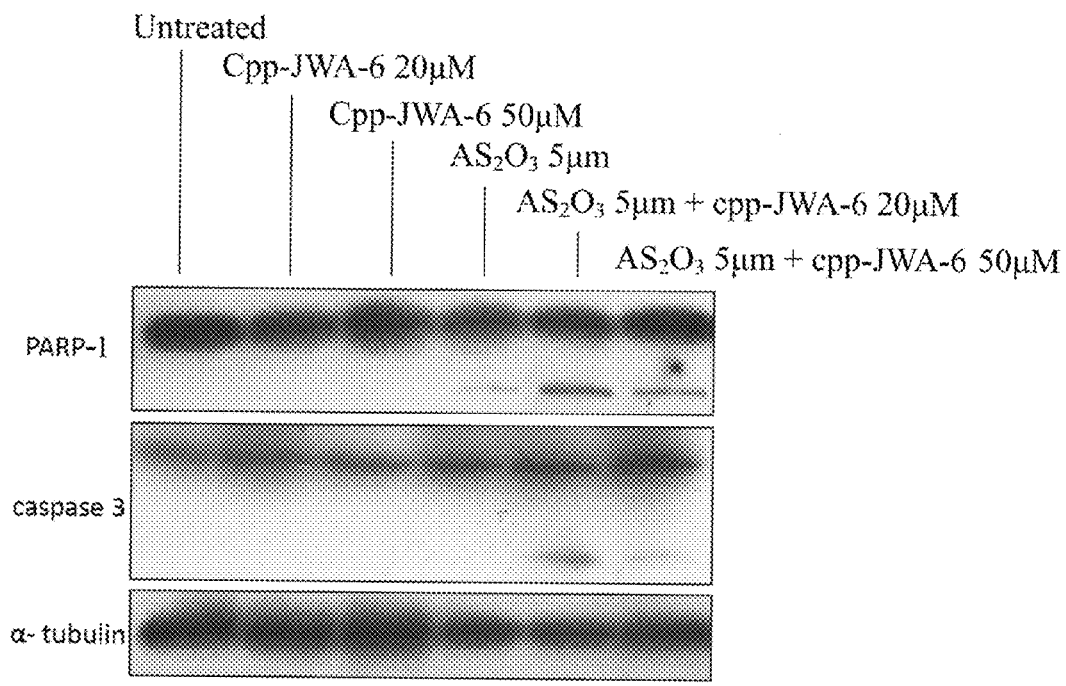
FIG. 40 illustrates a Western Blot assay showing changes in apoptosis-related molecules in Example 9.
Figure 41:
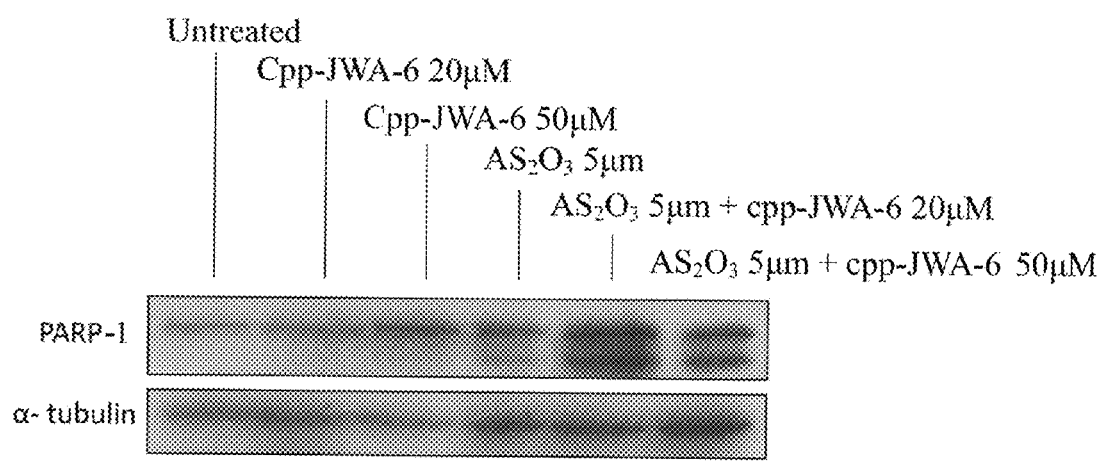
FIG. 41 illustrates a Western Blot assay showing changes in PARP-1 molecules in Example 9.

Polypeptide CPP-JWA-6 at a dose of 20 μM, 50 μM was applied individually and applied in combination with ATO (5 μM) on A375 cells (as shown in FIG. 40) and SGC7901 cells (as shown in FIG. 41) for 24 hrs before protein was extracted, and the Western Blot method of Example 7 was used to examine the changes in apoptosis-related molecules.

The results indicated that polypeptide CPP-JWA-6 at a dose not exceeding 50 μM will not cause any changes in the expression of PARP-1; in comparison with the single application of ATO, caspase-3 spliceosome and PARP-1 spliceosome were significantly increased after the combined action of CPP-JWA-6 and ATO, which indicated that polypeptide CPP-JWA-6 can also accelerate ATO-induced tumor apoptosis.

Example 10 Selecting Functional Polypeptides with Polypeptide JWA-6 as the Active Site The objective of this example was to select functional polypeptides from multiple combinations of sequences based on polypeptide JWA-6.

The mice with transplanted tumors in this example were the same as Example 2, and the experimental method used therein was also the same as Example 2. The various polypeptides were administered by intratumoral injection at a dose of 10 mg/kg, and a non-pep injection group (referred to simply as "non-pep group", the polypeptide sequence used was the same as Example 3) was established.

The sequences of various polypeptides were recorded as shown in Table 4.

TABLE 4

Sequences of various combinations of polypeptides

| Name | Amino Acid Sequence (N-terminus - C-terminus) | Phosphorylation Site | SEQ ID NO: |
|---|---|---|---|
| J1 | FPGSDRF | S phosphorylated | 15 |
| J2 | F-FPGSDRF | S phosphorylated | 31 |
| J3 | 6-aminocaproic acid-F-FPGSDRF | S phosphorylated | 32 |
| J4 | (R)$_9$-FPGSDRF | S phosphorylated | 33 |
| J5 | (R)$_9$-F-FPGSDRF | S phosphorylated | 34 |
| J6 | 6-aminocaproic acid-(R)$_9$-F-FPGSDRF | S phosphorylated | 35 |
| J7 | FPGSDRF-A | S phosphorylated | 36 |
| J8 | FPGSDRF-RGD | S phosphorylated | 37 |
| J9 | FPGSDRF-(G)$_4$-RGD | S phosphorylated | 38 |
| J10 | FPGSDRF-(G)$_{10}$-RGD | S phosphorylated | 39 |
| J11 | FPGSDRF-A-RGD | S phosphorylated | 40 |
| J12 | FPGSDRF-A-(G)$_4$-RGD | S phosphorylated | 41 |
| J13 | FPGSDRF-A-(G)$_{10}$-RGD | S phosphorylated | 42 |
| J14 | F-FPGSDRF-A | S phosphorylated | 43 |
| J15 | 6-aminocaproic acid-FPGSDRF-A | S phosphorylated | 44 |
| J16 | (R)$_9$-FPGSDRF-A | S phosphorylated | 45 |
| J17 | (R)$_9$-F-FPGSDRF-A | S phosphorylated | 46 |
| J18 | 6-aminocaproic acid-(R)$_9$-FPGSDRF-A | S phosphorylated | 47 |
| J19 | F-FPGSDRF-RGD | S phosphorylated | 48 |
| J20 | F-FPGSDRF-(G)$_4$-RGD | S phosphorylated | 49 |
| J21 | F-FPGSDRF-(G)$_{10}$-RGD | S phosphorylated | 50 |
| J22 | 6-aminocaproic acid-F-FPGSDRF-RGD | S phosphorylated | 51 |
| J23 | 6-aminocaproic acid-F-FPGSDRF-(G)$_4$-RGD | S phosphorylated | 52 |
| J24 | 6-aminocaproic acid-F-FPGSDRF-(G)$_{10}$-RGD | S phosphorylated | 53 |
| J25 | (R)$_9$-FPGSDRF-RGD | S phosphorylated | 54 |
| J26 | (R)$_9$-FPGSDRF-(G)$_4$-RGD | S phosphorylated | 55 |
| J27 | (R)$_9$-FPGSDRF-(G)$_{10}$-RGD | S phosphorylated | 56 |
| J28 | (R)$_9$-F-FPGSDRF-RGD | S phosphorylated | 57 |
| J29 | (R)$_9$-F-FPGSDRF-(G)$_4$-RGD | S phosphorylated | 58 |
| J30 | (R)$_9$-F-FPGSDRF-(G)$_{10}$-RGD | S phosphorylated | 59 |
| J31 | 6-aminocaproic acid-(R)$_9$-FPGSDRF-RGD | S phosphorylated | 60 |
| J32 | 6-aminocaproic acid-(R)$_9$-FPGSDRF-(G)$_4$-RGD | S phosphorylated | 61 |
| J33 | 6-aminocaproic acid-(R)$_9$-FPGSDRF-(G)$_{10}$-RGD | S phosphorylated | 62 |
| J34 | 6-aminocaproic acid-(R)$_9$-F-FPGSDRF-RGD | S phosphorylated | 63 |
| J35 | 6-aminocaproic acid-(R)$_9$-F-FPGSDRF-(G)$_4$-RGD | S phosphorylated | 64 |

TABLE 4-continued

Sequences of various combinations of polypeptides

| Name | Amino Acid Sequence (N-terminus - C-terminus) | Phosphorylation Site | SEQ ID NO: |
|---|---|---|---|
| J36 | 6-aminocaproic acid-(R)$_9$-F-FPGSDRF-(G)$_{10}$-RGD | S phosphorylated | 65 |
| J37 | F-FPGSDRF-A-RGD | S phosphorylated | 66 |
| J38 | F-FPGSDRF-A-(G)$_4$-RGD | S phosphorylated | 67 |
| J39 | F-FPGSDRF-A-(G)$_{10}$-RGD | S phosphorylated | 68 |
| J40 | 6-aminocaproic acid-FPGSDRF-A-RGD | S phosphorylated | 69 |
| J41 | 6-aminocaproic acid-FPGSDRF-A-(G)$_4$-RGD | S phosphorylated | 70 |
| J42 | 6-aminocaproic acid-FPGSDRF-A-(G)$_{10}$-RGD | S phosphorylated | 71 |
| J43 | 6-aminocaproic acid-F-FPGSDRF-A-RGD | S phosphorylated | 72 |
| J44 | 6-aminocaproic acid-F-FPGSDRF-A-(G)$_4$-RGD | S phosphorylated | 73 |
| J45 | 6-aminocaproic acid-F-FPGSDRF-A-(G)$_{10}$-RGD | S phosphorylated | 74 |
| J46 | (R)$_9$-FPGSDRF-A-RGD | S phosphorylated | 75 |
| J47 | (R)$_9$-FPGSDRF-A-(G)$_4$-RGD | S phosphorylated | 76 |
| J48 | (R)$_9$-FPGSDRF-A-(G)$_{10}$-RGD | S phosphorylated | 77 |
| J49 | (R)$_9$-F-FPGSDRF-A-RGD | S phosphorylated | 78 |
| J50 | (R)$_9$-F-FPGSDRF-A-(G)$_4$-RGD | S phosphorylated | 79 |
| J51 | (R)$_9$-F-FPGSDRF-A-(G)$_{10}$-RGD | S phosphorylated | 80 |
| J52 | 6-aminocaproic acid-(R)$_9$-FPGSDRF-A-RGD | S phosphorylated | 81 |
| J53 | 6-aminocaproic acid-(R)$_9$-FPGSDRF-A-(G)$_4$-RGD | S phosphorylated | 82 |
| J54 | 6-aminocaproic acid-(R)$_9$-FPGSDRF-A-(G)$_{10}$-RGD | S phosphorylated | 83 |
| J55 | 6-aminocaproic acid-(R)$_9$-F-FPGSDRF-A-RGD | S phosphorylated | 84 |
| J56 | 6-aminocaproic acid-(R)$_9$-F-FPGSDRF-A-(G)$_4$-RGD | S phosphorylated | 85 |
| J57 | 6-aminocaproic acid-(R)$_9$-F-FPGSDRF-A-(G)$_{10}$-RGD | S phosphorylated | 86 |

Because of space constraints, the actual experimental data is not listed herein. The experimental data indicated that polypeptides 1-57 have anti-tumor activity.

Unless otherwise indicated, the numerical ranges involved in the invention include the end values.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An anti-tumor polypeptide consisting of an amino acid sequence selected from the group consisting of:
FPGSDRF (SEQ ID NO: 15);
X-FPGSDRF (SEQ ID NO: 16);
FPGSDRF-Z (SEQ ID NO: 17); and
X-FPGSDRF-Z (SEQ ID NO: 18);
wherein
various capital letters denote amino acids as follows: F: phenylalanine; P: proline; G: glycine; D: aspartic acid; R: arginine;
S is a phosphorylated serine residue;
X and Z are an amino acid residue or an amino acid sequence, respectively;
X is one selected from the group consisting of F, $(R)_9$ (SEQ ID NO: 19), $(R)_9$-F (SEQ ID NO: 20), 6-aminocaproic acid, 6-aminocaproic acid-F, 6-aminocaproic acid-$(R)_9$ (SEQ ID NO: 21), and 6-aminocaproic acid-$(R)_9$-F (SEQ ID NO: 22);
Z is one selected from the group consisting of A, $(G)_n$-RGD (SEQ ID NO: 23), and A-$(G)_n$-RGD (SEQ ID NO: 24);
n is an integer greater than or equal to 0; and
the N-terminus of the polypeptide is acetylated and the C-terminus of the polypeptide is amidated.

2. An anti-tumor polypeptide consisting of an amino acid sequence selected from the group consisting of: FPGSDRF (SEQ ID NO: 15); X-FPGSDRF (SEQ ID NO: 16); FPGSDRF-Z (SEQ ID NO: 17); and X-FPGSDRF-Z (SEQ ID NO: 18); wherein various capital letters denote amino acids as follows: F: phenylalanine; P: proline; G: glycine; D: aspartic acid; R: arginine; S is a phosphorylated serine residue; X and Z are an amino acid residue or an amino acid sequence, respectively; X is one selected from the group consisting of F, $(R)_9$ (SEQ ID NO: 19), $(R)_9$-F (SEQ ID NO: 20), 6-aminocaproic acid, 6-aminocaproic acid-F, 6-aminocaproic acid-$(R)_9$ (SEQ ID NO: 21), and 6-aminocaproic acid-$(R)_9$-F (SEQ ID NO: 22); Z is one selected from the group consisting of A, $(G)_n$-RGD (SEQ ID NO: 23), and A-$(G)_n$-RGD (SEQ ID NO: 24); and n is between 0 and 10.

3. An anti-tumor polypeptide comprising an amino acid sequence selected from the group consisting of:
X-FPGSDRF (SEQ ID NO: 16);
FPGSDRF-Z (SEQ ID NO: 17); and
X-FPGSDRF-Z (SEQ ID NO: 18);
wherein
various capital letters denote amino acids as follows: F: phenylalanine; P: proline; G: glycine; D: aspartic acid; R: arginine;
S is a phosphorylated serine residue;
X and Z are an amino acid residue or an amino acid sequence, respectively;
X is one selected from the group consisting of $(R)_9$ (SEQ ID NO: 19), $(R)_9$-F (SEQ ID NO: 20), 6-aminocaproic acid, 6-aminocaproic acid-F, 6-aminocaproic acid-$(R)_9$ (SEQ ID NO: 21), and 6-aminocaproic acid-$(R)_9$-F (SEQ ID NO: 22);
Z is one selected from the group consisting of $(G)_n$-RGD (SEQ ID NO: 23), and A-$(G)_n$-RGD (SEQ ID NO: 24); and n is an integer greater than or equal to 0.

4. An anti-tumor polypeptide consisting of an amino acid sequence selected from the group consisting of: FPGSDRF (SEQ ID NO: 15); X-FPGSDRF (SEQ ID NO: 16); FPGSDRF-Z (SEQ ID NO: 17); and X-FPGSDRF-Z (SEQ ID NO: 18); wherein various capital letters denote amino acids as follows: F: phenylalanine; P: proline; G: glycine; D: aspartic acid; R: arginine; S is a phosphorylated serine residue; X and Z are an amino acid residue or an amino acid sequence, respectively; X is one selected from the group consisting of F, $(R)_9$ (SEQ ID NO: 19), $(R)_9$-F (SEQ ID NO: 20), 6-aminocaproic acid, 6-aminocaproic acid-F, 6-aminocaproic acid-$(R)_9$ (SEQ ID NO: 21), and 6-aminocaproic acid-$(R)_9$-F (SEQ ID NO: 22); Z is one selected from the group consisting of $(G)_n$-RGD (SEQ ID NO: 23), and A-$(G)_n$-RGD (SEQ ID NO: 24); and n is between 0 and 10.

* * * * *

```
                        SEQUENCE LISTING

<160> NUMBER OF SEQ ID NOS: 86

<210> SEQ ID NO 1
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 1

Xaa Phe Phe Pro Gly Ser Asp Arg Phe Ala
 1               5                  10

<210> SEQ ID NO 2
<211> LENGTH: 10
<212> TYPE: PRT
```

```
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 2

Xaa Phe Ile His Ala Ser Leu Arg Leu Arg
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 3

Xaa Leu Thr Asp Tyr Ile Ser Lys Val
1               5

<210> SEQ ID NO 4
<211> LENGTH: 6
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (4)..(4)
<223> OTHER INFORMATION: PHOSPHORYLATION

<400> SEQUENCE: 4

Xaa Pro Gly Ser Asp Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 5

Xaa Phe Pro Gly Ser Asp Arg Phe
1               5
```

```
<210> SEQ ID NO 6
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 6

Xaa Phe Phe Pro Gly Ser Asp Arg Phe Ala
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp, ACETYLATION
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (15)..(15)
<223> OTHER INFORMATION: AMIDATION

<400> SEQUENCE: 7

Xaa Phe Pro Gly Ser Asp Arg Phe Gly Gly Gly Gly Arg Gly Asp
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 8

Xaa Arg Arg Arg Arg Arg Arg Arg Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 9

Xaa Arg Lys Lys Arg Arg Gln Arg Arg Arg
1               5                   10

<210> SEQ ID NO 10
```

```
<211> LENGTH: 22
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 10

Xaa Lys Glu Thr Trp Trp Glu Thr Trp Trp Thr Glu Trp Ser Gln Pro
1               5                   10                  15

Lys Lys Lys Arg Lys Val
            20

<210> SEQ ID NO 11
<211> LENGTH: 12
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 11

Xaa Tyr Gly Arg Lys Lys Arg Arg Gln Arg Arg Arg
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 12

Xaa Arg Arg Arg Arg Arg Arg Arg Arg Phe Phe Pro Gly Ser Asp
1               5                   10                  15

Arg Phe Ala

<210> SEQ ID NO 13
<211> LENGTH: 17
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (14)..(14)
<223> OTHER INFORMATION: PHOSPHORYLATION

<400> SEQUENCE: 13

Xaa Arg Arg Arg Arg Arg Arg Arg Arg Phe Pro Gly Ser Asp Arg
1               5                   10                  15
```

Phe

```
<210> SEQ ID NO 14
<211> LENGTH: 6
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: ACETYLATION, Acp
<220> FEATURE:
<221> NAME/KEY: MOD_RES
<222> LOCATION: (6)..(6)
<223> OTHER INFORMATION: AMIDATION

<400> SEQUENCE: 14

Xaa Glu Glu Met Gln Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 15

Phe Pro Gly Ser Asp Arg Phe
1               5

<210> SEQ ID NO 16
<211> LENGTH: 8
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Xaa is F, RRRRRRRR, RRRRRRRR-F,
      6-aminocaproic acid, 6-aminocaproic acid-F, 6-aminocaproic
      acid-RRRRRRRR, or 6-aminocaproic acid-RRRRRRRR-F
<220> FEATURE:
<221> NAME/KEY: MOD_RES
<222> LOCATION: (5)..(5)
<223> OTHER INFORMATION: PHOSPHORYLATION

<400> SEQUENCE: 16

Xaa Phe Pro Gly Ser Asp Arg Phe
1               5

<210> SEQ ID NO 17
<211> LENGTH: 8
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (8)..(8)
<223> OTHER INFORMATION: Xaa is  A, (G)n-RGD, or A-(G)n-RGD, and n is
      an integer greater than or equal to 0
```

```
<400> SEQUENCE: 17

Phe Pro Gly Ser Asp Arg Phe Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Xaa is F, RRRRRRRRR, RRRRRRRR-F,
      6-aminocaproic acid, 6-aminocaproic acid-F, 6-aminocaproic
      acid-RRRRRRRRR, or 6-aminocaproic acid-RRRRRRRRR-F
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (9)..(9)
<223> OTHER INFORMATION: Xaa is  A, (G)n-RGD, or A-(G)n-RGD, and n
      is an integer greater than or equal to 0

<400> SEQUENCE: 18

Xaa Phe Pro Gly Ser Asp Arg Phe Xaa
1               5

<210> SEQ ID NO 19
<211> LENGTH: 9
<212> TYPE: PRT
<213> ORGANISM: Artificial Sequence
<220> FEATURE:
<223> OTHER INFORMATION: Fully synthetic

<400> SEQUENCE: 19

Arg Arg Arg Arg Arg Arg Arg Arg Arg
1               5

<210> SEQ ID NO 20
<211> LENGTH: 10
<212> TYPE: PRT
<213> ORGANISM: Artificial Sequence
<220> FEATURE:
<223> OTHER INFORMATION: Fully synthetic

<400> SEQUENCE: 20

Arg Arg Arg Arg Arg Arg Arg Arg Arg Phe
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 21

Xaa Arg Arg Arg Arg Arg Arg Arg Arg Arg
1               5                   10

<210> SEQ ID NO 22
```

```
<211> LENGTH: 11
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp

<400> SEQUENCE: 22

Xaa Arg Arg Arg Arg Arg Arg Arg Arg Arg Phe
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Fully synthetic
<220> FEATURE:
<221> NAME/KEY: REPEAT
<222> LOCATION: (1)..(1)
<223> OTHER INFORMATION: there is zero or several Gly

<400> SEQUENCE: 23

Gly Arg Gly Asp
1

<210> SEQ ID NO 24
<211> LENGTH: 5
<212> TYPE: PRT
<213> ORGANISM: Artificial Sequence
<220> FEATURE:
<223> OTHER INFORMATION: Fully synthetic
<220> FEATURE:
<221> NAME/KEY: REPEAT
<222> LOCATION: (2)..(2)
<223> OTHER INFORMATION: there is zero or several Gly

<400> SEQUENCE: 24

Ala Gly Arg Gly Asp
1               5

<210> SEQ ID NO 25
<211> LENGTH: 4
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (3)..(3)
<223> OTHER INFORMATION: PHOSPHORYLATION

<400> SEQUENCE: 25

Xaa Gly Ser Asp
1

<210> SEQ ID NO 26
<211> LENGTH: 11
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
```

```
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 26

Xaa Phe Pro Gly Ser Asp Arg Phe Arg Gly Asp
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 27

Xaa Phe Pro Gly Ser Asp Arg Phe Gly Arg Gly Asp
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 28

Xaa Phe Pro Gly Ser Asp Arg Phe Gly Gly Gly Arg Gly Asp
1               5                   10

<210> SEQ ID NO 29
<211> LENGTH: 18
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 29

Xaa Phe Pro Gly Ser Asp Arg Phe Gly Gly Gly Gly Gly Gly Arg
1               5                   10                  15

Gly Asp

<210> SEQ ID NO 30
```

```
<211> LENGTH: 20
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 30

Phe Pro Gly Ser Asp Arg Phe Gly Gly Gly Gly Gly Gly Gly Gly
1               5                   10                  15

Gly Arg Gly Asp
            20

<210> SEQ ID NO 31
<211> LENGTH: 8
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 31

Phe Phe Pro Gly Ser Asp Arg Phe
1               5

<210> SEQ ID NO 32
<211> LENGTH: 9
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 32

Xaa Phe Phe Pro Gly Ser Asp Arg Phe
1               5

<210> SEQ ID NO 33
<211> LENGTH: 16
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)
<223> OTHER INFORMATION: PHOSPHORYLATION

<400> SEQUENCE: 33

Arg Arg Arg Arg Arg Arg Arg Arg Phe Pro Gly Ser Asp Arg Phe
1               5                   10                  15

<210> SEQ ID NO 34
```

```
<211> LENGTH: 17
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (14)..(14)
<223> OTHER INFORMATION: PHOSPHORYLATION

<400> SEQUENCE: 34

Arg Arg Arg Arg Arg Arg Arg Arg Arg Phe Phe Pro Gly Ser Asp Arg
1               5                   10                  15

Phe

<210> SEQ ID NO 35
<211> LENGTH: 18
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 35

Xaa Arg Arg Arg Arg Arg Arg Arg Arg Phe Phe Pro Gly Ser Asp
1               5                   10                  15

Arg Phe

<210> SEQ ID NO 36
<211> LENGTH: 8
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 36

Phe Pro Gly Ser Asp Arg Phe Ala
1               5

<210> SEQ ID NO 37
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 37

Phe Pro Gly Ser Asp Arg Phe Arg Gly Asp
1               5                   10

<210> SEQ ID NO 38
<211> LENGTH: 14
<212> TYPE: PRT
<213> ORGANISM: Artificial Sequence
```

```
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 38

Phe Pro Gly Ser Asp Arg Phe Gly Gly Gly Gly Arg Gly Asp
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 39

Phe Pro Gly Ser Asp Arg Phe Gly Gly Gly Gly Gly Gly Gly Gly
1               5                   10                  15

Gly Arg Gly Asp
            20

<210> SEQ ID NO 40
<211> LENGTH: 11
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 40

Phe Pro Gly Ser Asp Arg Phe Ala Arg Gly Asp
1               5                   10

<210> SEQ ID NO 41
<211> LENGTH: 15
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 41

Phe Pro Gly Ser Asp Arg Phe Ala Gly Gly Gly Arg Gly Asp
1               5                   10                  15

<210> SEQ ID NO 42
<211> LENGTH: 21
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (4)..(4)
<223> OTHER INFORMATION: PHOSPHORYLATION

<400> SEQUENCE: 42
```

```
Phe Pro Gly Ser Asp Arg Phe Ala Gly Gly Gly Gly Gly Gly Gly
1               5                   10                  15

Gly Gly Arg Gly Asp
            20

<210> SEQ ID NO 43
<211> LENGTH: 9
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 43

Phe Phe Pro Gly Ser Asp Arg Phe Ala
1               5

<210> SEQ ID NO 44
<211> LENGTH: 10
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 44

Xaa Phe Phe Pro Gly Ser Asp Arg Phe Ala
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)
<223> OTHER INFORMATION: PHOSPHORYLATION

<400> SEQUENCE: 45

Arg Arg Arg Arg Arg Arg Arg Arg Arg Phe Pro Gly Ser Asp Arg Phe
1               5                   10                  15

Ala

<210> SEQ ID NO 46
<211> LENGTH: 18
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (14)..(14)
<223> OTHER INFORMATION: PHOSPHORYLATION

<400> SEQUENCE: 46

Arg Arg Arg Arg Arg Arg Arg Arg Arg Phe Phe Pro Gly Ser Asp Arg
```

```
1               5                   10                  15

Phe Ala

<210> SEQ ID NO 47
<211> LENGTH: 18
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 47

Xaa Arg Arg Arg Arg Arg Arg Arg Arg Phe Pro Gly Ser Asp Arg
1               5                   10                  15

Phe Ala

<210> SEQ ID NO 48
<211> LENGTH: 11
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 48

Phe Phe Pro Gly Ser Asp Arg Phe Arg Gly Asp
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 49

Phe Phe Pro Gly Ser Asp Arg Phe Gly Gly Gly Gly Arg Gly Asp
1               5                   10                  15

<210> SEQ ID NO 50
<211> LENGTH: 21
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 50
```

-continued

```
Phe Phe Pro Gly Ser Asp Arg Phe Gly Gly Gly Gly Gly Gly
1               5                   10                  15

Gly Gly Arg Gly Asp
            20

<210> SEQ ID NO 51
<211> LENGTH: 12
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 51

Xaa Phe Phe Pro Gly Ser Asp Arg Phe Arg Gly Asp
1               5                   10

<210> SEQ ID NO 52
<211> LENGTH: 16
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 52

Xaa Phe Phe Pro Gly Ser Asp Arg Phe Gly Gly Gly Arg Gly Asp
1               5                   10                  15

<210> SEQ ID NO 53
<211> LENGTH: 22
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 53

Xaa Phe Phe Pro Gly Ser Asp Arg Phe Gly Gly Gly Gly Gly Gly
1               5                   10                  15

Gly Gly Gly Arg Gly Asp
            20

<210> SEQ ID NO 54
<211> LENGTH: 19
<212> TYPE: PRT
<213> ORGANISM: Artificial Sequence
<220> FEATURE:
<223> OTHER INFORMATION: Fully synthetic
```

```
<220> FEATURE:
<221> NAME/KEY: MOD_RES
<222> LOCATION: (13)..(13)
<223> OTHER INFORMATION: PHOSPHORYLATION

<400> SEQUENCE: 54

Arg Arg Arg Arg Arg Arg Arg Arg Arg Phe Pro Gly Ser Asp Arg Phe
1               5                   10                  15

Arg Gly Asp

<210> SEQ ID NO 55
<211> LENGTH: 23
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)
<223> OTHER INFORMATION: PHOSPHORYLATION

<400> SEQUENCE: 55

Arg Arg Arg Arg Arg Arg Arg Arg Arg Phe Pro Gly Ser Asp Arg Phe
1               5                   10                  15

Gly Gly Gly Gly Arg Gly Asp
            20

<210> SEQ ID NO 56
<211> LENGTH: 29
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)
<223> OTHER INFORMATION: PHOSPHORYLATION

<400> SEQUENCE: 56

Arg Arg Arg Arg Arg Arg Arg Arg Arg Phe Pro Gly Ser Asp Arg Phe
1               5                   10                  15

Gly Gly Gly Gly Gly Gly Gly Gly Gly Gly Arg Gly Asp
            20                  25

<210> SEQ ID NO 57
<211> LENGTH: 20
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (14)..(14)
<223> OTHER INFORMATION: PHOSPHORYLATION

<400> SEQUENCE: 57

Arg Arg Arg Arg Arg Arg Arg Arg Arg Phe Phe Pro Gly Ser Asp Arg
1               5                   10                  15

Phe Arg Gly Asp
            20

<210> SEQ ID NO 58
<211> LENGTH: 24
<212> TYPE: PRT
<213> ORGANISM: Artificial Sequence
<220> FEATURE:
<223> OTHER INFORMATION: Fully synthetic
```

```
<220> FEATURE:
<221> NAME/KEY: MOD_RES
<222> LOCATION: (14)..(14)
<223> OTHER INFORMATION: PHOSPHORYLATION

<400> SEQUENCE: 58

Arg Arg Arg Arg Arg Arg Arg Arg Phe Phe Pro Gly Ser Asp Arg
1               5                   10                  15

Phe Gly Gly Gly Gly Arg Gly Asp
            20

<210> SEQ ID NO 59
<211> LENGTH: 30
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (14)..(14)
<223> OTHER INFORMATION: PHOSPHORYLATION

<400> SEQUENCE: 59

Arg Arg Arg Arg Arg Arg Arg Arg Phe Phe Pro Gly Ser Asp Arg
1               5                   10                  15

Phe Gly Gly Gly Gly Gly Gly Gly Gly Gly Arg Gly Asp
            20                  25                  30

<210> SEQ ID NO 60
<211> LENGTH: 20
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 60

Xaa Arg Arg Arg Arg Arg Arg Arg Arg Phe Pro Gly Ser Asp Arg
1               5                   10                  15

Phe Arg Gly Asp
            20

<210> SEQ ID NO 61
<211> LENGTH: 24
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 61

Xaa Arg Arg Arg Arg Arg Arg Arg Arg Phe Pro Gly Ser Asp Arg
1               5                   10                  15

Phe Gly Gly Gly Gly Arg Gly Asp
```

-continued

```
                20

<210> SEQ ID NO 62
<211> LENGTH: 30
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 62

Xaa Arg Arg Arg Arg Arg Arg Arg Arg Phe Pro Gly Ser Asp Arg
1               5                   10                  15

Phe Gly Gly Gly Gly Gly Gly Gly Gly Gly Arg Gly Asp
            20                  25                  30

<210> SEQ ID NO 63
<211> LENGTH: 21
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 63

Xaa Arg Arg Arg Arg Arg Arg Arg Arg Phe Phe Pro Gly Ser Asp
1               5                   10                  15

Arg Phe Arg Gly Asp
            20

<210> SEQ ID NO 64
<211> LENGTH: 25
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 64

Xaa Arg Arg Arg Arg Arg Arg Arg Arg Phe Phe Pro Gly Ser Asp
1               5                   10                  15

Arg Phe Gly Gly Gly Gly Arg Gly Asp
            20                  25

<210> SEQ ID NO 65
<211> LENGTH: 31
<212> TYPE: PRT
<213> ORGANISM: Artificial Sequence
```

```
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 65

Xaa Arg Arg Arg Arg Arg Arg Arg Arg Phe Phe Pro Gly Ser Asp
1               5                   10                  15

Arg Phe Gly Gly Gly Gly Gly Gly Gly Gly Gly Arg Gly Asp
            20                  25                  30

<210> SEQ ID NO 66
<211> LENGTH: 12
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 66

Phe Phe Pro Gly Ser Asp Arg Phe Ala Arg Gly Asp
1               5                   10

<210> SEQ ID NO 67
<211> LENGTH: 16
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 67

Phe Phe Pro Gly Ser Asp Arg Phe Ala Gly Gly Gly Gly Arg Gly Asp
1               5                   10                  15

<210> SEQ ID NO 68
<211> LENGTH: 22
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (5)..(5)
<223> OTHER INFORMATION: PHOSPHORYLATION

<400> SEQUENCE: 68

Phe Phe Pro Gly Ser Asp Arg Phe Ala Gly Gly Gly Gly Gly Gly
1               5                   10                  15

Gly Gly Gly Arg Gly Asp
            20

<210> SEQ ID NO 69
<211> LENGTH: 12
<212> TYPE: PRT
<213> ORGANISM: Artificial Sequence
<220> FEATURE:
```

```
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 69

Xaa Phe Pro Gly Ser Asp Arg Phe Ala Arg Gly Asp
 1               5                  10

<210> SEQ ID NO 70
<211> LENGTH: 16
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 70

Xaa Phe Pro Gly Ser Asp Arg Phe Ala Gly Gly Gly Gly Arg Gly Asp
 1               5                  10                  15

<210> SEQ ID NO 71
<211> LENGTH: 22
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (5)..(5)
<223> OTHER INFORMATION: PHOSPHORYLATION

<400> SEQUENCE: 71

Xaa Phe Pro Gly Ser Asp Arg Phe Ala Gly Gly Gly Gly Gly Gly Gly
 1               5                  10                  15

Gly Gly Gly Arg Gly Asp
             20

<210> SEQ ID NO 72
<211> LENGTH: 13
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 72

Xaa Phe Phe Pro Gly Ser Asp Arg Phe Ala Arg Gly Asp
```

<210> SEQ ID NO 73
<211> LENGTH: 17
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 73

Xaa Phe Phe Pro Gly Ser Asp Arg Phe Ala Gly Gly Gly Gly Arg Gly
1               5                   10                  15

Asp

<210> SEQ ID NO 74
<211> LENGTH: 23
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (6)..(6)
<223> OTHER INFORMATION: PHOSPHORYLATION

<400> SEQUENCE: 74

Xaa Phe Phe Pro Gly Ser Asp Arg Phe Ala Gly Gly Gly Gly Gly Gly
1               5                   10                  15

Gly Gly Gly Gly Arg Gly Asp
            20

<210> SEQ ID NO 75
<211> LENGTH: 20
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)
<223> OTHER INFORMATION: PHOSPHORYLATION

<400> SEQUENCE: 75

Arg Arg Arg Arg Arg Arg Arg Arg Arg Phe Pro Gly Ser Asp Arg Phe
1               5                   10                  15

Ala Arg Gly Asp
            20

<210> SEQ ID NO 76
<211> LENGTH: 24
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)

<223> OTHER INFORMATION: PHOSPHORYLATION

<400> SEQUENCE: 76

Arg Arg Arg Arg Arg Arg Arg Arg Arg Phe Pro Gly Ser Asp Arg Phe
1               5                   10                  15

Ala Gly Gly Gly Gly Arg Gly Asp
            20

<210> SEQ ID NO 77
<211> LENGTH: 30
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (13)..(13)
<223> OTHER INFORMATION: PHOSPHORYLATION

<400> SEQUENCE: 77

Arg Arg Arg Arg Arg Arg Arg Arg Arg Phe Pro Gly Ser Asp Arg Phe
1               5                   10                  15

Ala Gly Gly Gly Gly Gly Gly Gly Gly Gly Gly Arg Gly Asp
            20                  25                  30

<210> SEQ ID NO 78
<211> LENGTH: 21
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (14)..(14)
<223> OTHER INFORMATION: PHOSPHORYLATION

<400> SEQUENCE: 78

Arg Arg Arg Arg Arg Arg Arg Arg Arg Phe Phe Pro Gly Ser Asp Arg
1               5                   10                  15

Phe Ala Arg Gly Asp
            20

<210> SEQ ID NO 79
<211> LENGTH: 25
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (14)..(14)
<223> OTHER INFORMATION: PHOSPHORYLATION

<400> SEQUENCE: 79

Arg Arg Arg Arg Arg Arg Arg Arg Arg Phe Phe Pro Gly Ser Asp Arg
1               5                   10                  15

Phe Ala Gly Gly Gly Gly Arg Gly Asp
            20                  25

<210> SEQ ID NO 80
<211> LENGTH: 31
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES -continued

```
<222> LOCATION: (14)..(14)
<223> OTHER INFORMATION: PHOSPHORYLATION

<400> SEQUENCE: 80

Arg Arg Arg Arg Arg Arg Arg Arg Arg Phe Phe Pro Gly Ser Asp Arg
1               5                   10                  15

Phe Ala Gly Gly Gly Gly Gly Gly Gly Gly Gly Arg Gly Asp
            20                  25                  30

<210> SEQ ID NO 81
<211> LENGTH: 21
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (14)..(14)
<223> OTHER INFORMATION: PHOSPHORYLATION

<400> SEQUENCE: 81

Xaa Arg Arg Arg Arg Arg Arg Arg Arg Phe Pro Gly Ser Asp Arg
1               5                   10                  15

Phe Ala Arg Gly Asp
            20

<210> SEQ ID NO 82
<211> LENGTH: 25
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (14)..(14)
<223> OTHER INFORMATION: PHOSPHORYLATION

<400> SEQUENCE: 82

Xaa Arg Arg Arg Arg Arg Arg Arg Arg Phe Pro Gly Ser Asp Arg
1               5                   10                  15

Phe Ala Gly Gly Gly Gly Arg Gly Asp
            20                  25

<210> SEQ ID NO 83
<211> LENGTH: 31
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (14)..(14)
<223> OTHER INFORMATION: PHOSPHORYLATION

<400> SEQUENCE: 83

Xaa Arg Arg Arg Arg Arg Arg Arg Arg Phe Pro Gly Ser Asp Arg
1               5                   10                  15
```

```
Phe Ala Gly Gly Gly Gly Gly Gly Gly Gly Arg Gly Asp
        20                  25                  30

<210> SEQ ID NO 84
<211> LENGTH: 22
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 84

Xaa Arg Arg Arg Arg Arg Arg Arg Arg Phe Phe Pro Gly Ser Asp
1               5                   10                  15

Arg Phe Ala Arg Gly Asp
            20

<210> SEQ ID NO 85
<211> LENGTH: 26
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 85

Xaa Arg Arg Arg Arg Arg Arg Arg Arg Phe Phe Pro Gly Ser Asp
1               5                   10                  15

Arg Phe Ala Gly Gly Gly Gly Arg Gly Asp
            20                  25

<210> SEQ ID NO 86
<211> LENGTH: 32
<212> TYPE: PRT
<213> ORGANISM: Artificial Sequence
<220> FEATURE:
<223> OTHER INFORMATION: Fully synthetic
<220> FEATURE:
<221> NAME/KEY: MOD_RES
<222> LOCATION: (1)..(1)
<223> OTHER INFORMATION: Acp
<220> FEATURE:
<221> NAME/KEY: MOD_RES
<222> LOCATION: (15)..(15)
<223> OTHER INFORMATION: PHOSPHORYLATION

<400> SEQUENCE: 86

Xaa Arg Arg Arg Arg Arg Arg Arg Arg Phe Phe Pro Gly Ser Asp
1               5                   10                  15

Arg Phe Ala Gly Gly Gly Gly Gly Gly Gly Gly Arg Gly Asp
            20                  25                  30
```